United States Patent
Chabala et al.

(10) Patent No.: US 10,111,862 B2
(45) Date of Patent: Oct. 30, 2018

(54) TRAPS IN THE TREATMENT OF MACULAR DEGENERATION

(71) Applicant: Aldeyra Therapeutics, Inc., Lexington, MA (US)

(72) Inventors: John Clifford Chabala, Scotch Plains, NJ (US); Thomas A. Jordan, Lexington, MA (US); Ke-Qing Ling, Painesville, OH (US); John G. Gleason, The Villages, FL (US); William A. Kinney, Newtown, PA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

(21) Appl. No.: 14/760,041

(22) PCT Filed: Jan. 21, 2014

(86) PCT No.: PCT/US2014/012356
§ 371 (c)(1),
(2) Date: Jul. 9, 2015

(87) PCT Pub. No.: WO2014/116593
PCT Pub. Date: Jul. 31, 2014

(65) Prior Publication Data
US 2015/0344447 A1    Dec. 3, 2015

Related U.S. Application Data

(60) Provisional application No. 61/756,778, filed on Jan. 25, 2013.

(51) Int. Cl.
| | | |
|---|---|---|
| *C07D 261/20* | (2006.01) | |
| *C07D 263/57* | (2006.01) | |
| *A61K 31/421* | (2006.01) | |

(52) U.S. Cl.
CPC .......... *A61K 31/421* (2013.01); *C07D 261/20* (2013.01); *C07D 263/57* (2013.01)

(58) Field of Classification Search
None
See application file for complete search history.

(56) References Cited

U.S. PATENT DOCUMENTS

| | | | |
|---|---|---|---|
| 2,086,186 | A | 7/1937 | Messer |
| 3,912,748 | A | 10/1975 | Evans et al. |
| 5,472,954 | A | 12/1995 | Loftsson |
| 5,493,027 | A | 2/1996 | Nichols et al. |
| 5,668,117 | A | 9/1997 | Shapiro |
| 5,742,954 | A | 4/1998 | Idland |
| 6,191,127 | B1 | 2/2001 | Holscher |
| 6,444,221 | B1 | 9/2002 | Shapiro |
| 6,498,154 | B1 | 12/2002 | Grubb |
| 6,569,879 | B2 * | 5/2003 | Liu ........................ A61K 31/00 514/373 |
| 7,297,709 | B2 | 11/2007 | Dai et al. |
| 7,531,564 | B2 | 5/2009 | Malamas et al. |
| 7,973,025 | B2 | 7/2011 | Jordan |
| 7,982,071 | B2 | 7/2011 | Scott |
| 8,940,721 | B2 | 1/2015 | Jordan |
| 8,940,764 | B2 | 1/2015 | Jordan |
| 9,687,481 | B2 * | 6/2017 | Brady ...................... A61K 8/49 |
| 2004/0132636 | A1 | 7/2004 | Dooley |
| 2004/0235892 | A1 | 11/2004 | Dai et al. |
| 2005/0020603 | A1 | 1/2005 | Dai |
| 2005/0090553 | A1 | 4/2005 | Shapiro |
| 2005/0130906 | A1 | 6/2005 | Matier |
| 2005/0197292 | A1 | 9/2005 | Smithson |
| 2005/0234018 | A1 | 10/2005 | Lyons |
| 2006/0111318 | A1 | 5/2006 | Okamoto |
| 2006/0183909 | A1 | 8/2006 | Schmitt et al. |
| 2006/0189608 | A1 | 8/2006 | Bingaman |
| 2007/0129404 | A1 | 6/2007 | Hagihara |
| 2007/0135481 | A1 | 6/2007 | Jordan |
| 2012/0108585 | A1 | 5/2012 | Vu |

(Continued)

FOREIGN PATENT DOCUMENTS

| | | | |
|---|---|---|---|
| EP | | 0186367 A2 | 7/1986 |
| EP | | 0245054 A1 | 11/1987 |

(Continued)

OTHER PUBLICATIONS

Search Report and Written Opinion issued by the Intellectual Property Office of Singapore for Singapore Patent Application No. 11201505599Y, dated Sep. 14, 2016 (5 pages).

Aldini et al., "Lipoxidation-Derived Reactive Carbonyl Species as Potential Drug Targets in Preventing Protein Carbonylation and Related Cellular Dysfunction," *Chem Med Chem*, 1(10):1045-1058 (2006).

Burcham et al., "Aldehyde-Sequestering Drugs: Tools for Studying Protein Damage by Lipid Peroxidation Products," *Toxicology*, 181-182: 229-236 (2002).

Negre-Salvayre et al., "Advanced Lipid Peroxidation End Products in Oxidative Damage to Proteins. Potential Role in Diseases and Therapeutic Prospects for the Inhibitors," *British Journal of Pharmacology*, 153(1):6-20 (2008).

(Continued)

*Primary Examiner* — Nyeemah A Grazier
(74) *Attorney, Agent, or Firm* — Andrea L. C. Reid; Dechert LLP

(57) ABSTRACT

The present invention is directed to compounds of formula (A):

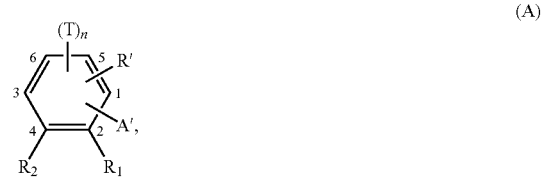

pharmaceutical compositions, and methods of use for treating, reducing a symptom of or reducing the risk of macular degeneration.

24 Claims, 1 Drawing Sheet

(56) References Cited

U.S. PATENT DOCUMENTS

| | | | |
|---|---|---|---|
| 2012/0302601 A1* | 11/2012 | Jordan | A61K 9/0048 514/313 |
| 2015/0209333 A1 | 7/2015 | Jordan | |
| 2015/0209345 A1 | 7/2015 | Jordan | |
| 2015/0335632 A1 | 11/2015 | Brady | |
| 2015/0344432 A1 | 12/2015 | Jordan | |
| 2017/0239196 A1* | 8/2017 | Brady | A61K 31/137 |

FOREIGN PATENT DOCUMENTS

| | | |
|---|---|---|
| EP | 0483881 A1 | 5/1992 |
| EP | 1621199 A1 | 1/2006 |
| EP | 2301549 A1 | 3/2011 |
| EP | 1888548 B1 | 8/2012 |
| JP | 2007532648 A | 11/2007 |
| JP | 2008542291 A | 11/2008 |
| SU | 509046 A1 | 6/1984 |
| WO | WO1996/022992 A1 | 8/1996 |
| WO | WO1999/046237 A1 | 9/1999 |
| WO | WO2001/041757 A1 | 6/2001 |
| WO | WO2004/082622 A2 | 9/2004 |
| WO | WO2004/091630 A1 | 10/2004 |
| WO | WO2005/035506 A1 | 4/2005 |
| WO | WO2005/079774 A2 | 9/2005 |
| WO | WO2005/105067 A2 | 11/2005 |
| WO | WO-2006002473 A1 | 1/2006 |
| WO | WO2006/049968 A1 | 5/2006 |
| WO | WO2006/127945 A1 | 11/2006 |
| WO | WO2007/118276 A1 | 10/2007 |
| WO | WO2008/014602 A1 | 2/2008 |
| WO | WO2010/133672 A1 | 11/2010 |
| WO | WO-2011008202 A1 | 1/2011 |
| WO | WO-2011071995 A2 | 6/2011 |
| WO | WO 2011072141 A1 * | 6/2011 ........... A61K 9/0048 |
| WO | WO-2012097173 A2 | 7/2012 |
| WO | WO-2012105887 A1 | 8/2012 |
| WO | WO2014/100425 A1 | 7/2014 |
| WO | WO2014/116836 A1 | 7/2014 |

OTHER PUBLICATIONS

Supplementary Partial European Search Report issued by the European Patent Office for European Patent Application No. 14743711.5, dated Jul. 20, 2016 (14 pages).

Search Report and Written Opinion issued by the Intellectual Property Office of Singapore for Singapore Patent Application No. 11201505587Y, dated Jul. 12, 2016 (12 pages).

Voziyan et al., "A Post-Amadori Inhibitor Pyridoxamine also Inhibits Chemical Modification of Proteins by Scavenging Carbonyl Intermediates for Carbohydrate and Lipid Degradation," *Journal of Biological Chemistry*, 277(5): 3397-3403 (2002).

Wood et al., "Aldehyde Load in Ischemia-Reperfusion Brain Injury: Neuroprotection by Neutralization of reactive Aldehydes with Phenelzine," *Brain Research*, 1122(1): 184-190 (2006).

Zagol-Ikapitte et al., "Characterization of scavengers of γ-ketoaldehydes that do not inhibit prostaglandin biosynthesis," *Chemical Research in Toxicology*, 23(1): 240-250 (2010).

Atkinson et al., 1966, "Triazaphenanthrenes. Part VI Further Observations on the Widman-Stoermer and Brosche Reactions," Journal of Chemical Society, pp. 2053-2060.

Godard et al., 1980, "Sur les orthoamino formyl quinoléines, nouveaux synthons hétérocycliques," Journal of Heterocyclic Chemistry, 17(3):465-473.

Grob et al., 1950, "Die Synthese von 5-Oxy-benz(cd)indolin und dessen Umpagerung in 5-Keto-1,3,4,5-tetrahydro-benz(cd)indol," Helvetica Chimica Acta, Verlag Helvetica Chimica Acta, Ch, 33(6):1796-1808.

Supplementary European Search Report issued by the European Patent Office for European Patent Application No. EP13865015.5 dated Mar. 31, 2016 (9 pages).

Tian et al., 2012, "First total synthesis and determination of the absolute configuration of 1-N-methyl-3-methylamino[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895.

Acland et al., "Gene Therapy Restores Vision in Canine Model of Childhood Blindness," Nature Genetics, 28:92-95 (2001).

Bernstein et al., "Retinal Toxicity Associated with Occupational Exposure to the Fish Anesthetic MS-222," American Journal of Ophthalmology, 124(6):843-844 (1997).

Bernstein et al., "Mechanism of Action of Aromatic Amines that Short Circuit the Visual Cycle," Biochemistry, 25:3370-3377 (1986).

Bernstein et al., "Short Circuiting the Visual Cycle with Retinotoxic Aromatic Amines," Proc Natl Acad Sci USA, 83:1632-1635 (1986).

Bernstein et al., "The Specific Inhibition of 11 cis-Retinyl Palmitate Formation in the Frog Eye by Diaminophenopentane, an Inhibitor of Rhodopsin Regeneration," Vision Research, 25(6):741-748 (1985).

Bucciantini et al., "Inherent Toxicity of Aggregates Implies a Common Mechanism for Protein Misfolding Diseases," Nature, 416:507-511 (2002).

Chapple et al., "Unfolding Retinal Dystrophies: A Role for Molecular Chaperones," Trends in Molecular Medicine, 7(9):414-421 (2001).

Conover et al., "Thiazole analogs of pyridoxine, Journal of the American Chemical Society, 72(110:5221-5225 (1950).

De Jong, Paulus, "Age-Related Macular Degeneration," The New England Journal of Medicine, 355:1474-1485 (2006).

Dowling J.E., "Neural and Photochemical Mechanisms of Visual Adaptation in the Rat," Journal of General Physiology, 46:1287-1301 (2006).

Drysdale et al., "Complex Promoter and Coding Region β2-Adrenergic Receptor Haplotypes Alter Receptor Expression and Predict in vivo Responsiveness," Proceedings of the National Academy of Sciences USA, 97(19):10483-10488 (2000).

Fowler et al., "Colored Complexes of all-trans-retinal with Bezocaine and Other Local Anesthetics," Journal of Photochemistry and Photobiology B: Biology, 8:183-188 (1991).

Hubbard, R., "Geometical Isomerization of Vitamin A, Retinene and Retinine Oxime," Journal of the American Chemical Society, 78:4662-4667 (1956).

Hurd et al., "Reaction of propiolactone with aniline derivatives," Journal of the American Chemical Society, 74:5889-5891 (1952).

Ito, N. et al., "A medium-term rat liver bioassay for rapid in vivo detection of carcinogenic potential of chemicals, Cancer Science", 94(1):3-8 (2003).

Karan et al., "Lipofuscin accumulation, abnormal electrophysiology, and photoreceptor degeneration in mutant ELOVL4 transgenic mic: a model for macular degeneration," Proceedings of the National Academy of Sciences USA, 102(11):4164-4169 (2005).

Landor, S. et al., "Allenes. Part 49. 1 4-Amino-2-(1 hydroxyalkyl) quinolines from PHenylhdroxylamine and Allenic Nitriles," J Chem Soc., Perkin Trans, 251-254 (1989).

Li et al., "Effect of Vitamin A supplementation on rhodopsin mutants threonine-17→methionine and proline-347→serine in transgenic mice and in cell cultures," Proc. Natl. Acad. Sci. USA 95:11933-11938 (1998).

Nema et al., "Excipients and Their Use in Injectable Products," PDA Journal of Pharmaceutical Science and Technology, 51(4): 166-171 (1997).

Nerurkar et al., "β-arylglutaconic acids. II. Imides of certain P-arylglutaconic and glutaric acids," Journal of Organic Chemistry, 24:2055-2056 (1959).

Noorwez et al., "Pharmacological chaperone-mediated in vivo folding and stabilization of the P23H-opsin mutant associated with autosomal dominant retinitis pigmentosa," Journal of Biological Chemistry, 278(16):14442-14450 (2003).

Organisciak et al., "Susceptability to retinal light damage in transgenic rats with rhodopsin mutations," Investigative Ophthalmology & Visual Science, 44:486-492 (2003).

Parish et al., "Isolation and one-step preparation of A2E and iso-A2E, fluorophorcs from human retinal pigment epithelium," Proceedings of the National Academy of Sciences USA, 95:14609-14613 (1998).

(56) References Cited

OTHER PUBLICATIONS

Radu et al., "Treatment with isoretinin inhibits lipofuscin accumulation in a mouse model of recessive Stargardt's macular degeneration," Proc Natl Acad Sci. USA, 100(8):4742-4747 (2003).
Rapp et al., "The effects of local anesthetics on retinal function," Vision Research, 22:1097-1103 (1982).
Sherman et al., "Cellular defenses against unfolded proteins: a cell biologist thinks about neurodegenerative diseases," Neuron, 29:15-32 (2001).
Sieving et al., "Inhibition of the visual cycle in vivo by 12-cis retinoic acid protects from light damage and provides a mechanism for night blindness in isoretinin therapy," Proceedings of the National Academy of Sciences USA, 98(4):1835-1840 (2001).
Snell et al., "Novel structure having antagonist actions at both the glycine site of the N-Methyl-DAspartate receptor and neuronal voltage-sensitive sodium channels: biochemical, electrophysiological, and behavioral characterization," Journal of Pharmacology and Experimental Therapeutics, 292(0:215-227 (2000).
Ueda et al., "Evaluation of sulfobutyl ether beta-cyclodextrin as a stabilizing/solubilizing agent for several drugs," Drug Dev. Ind. Pharm. 24:863-7 (1998).
Vlaskina et al., "Novel synthesis of substituted benzimidazoles by reduction of esters of 4-alkylamino-3, 5-dinitro-benzoic acids by tin chloride," Chemistry of Heterocyclic Compounds, 40(4):523-524 (2004).
Wang et al., "A facile one-pot synthesis of 2-substituted-3-aminoquinolincs: preparation of benzo[b]naphthyridine-3-carbonitriles,"Tetrahedron, 60(13):2937-2942 (2004).

Weng et al., "Insights into the function of Rim protein in photoreceptors and etiology of Stargardt's disease from the phenotype in abcr knockout mice," Cell, 98:13-23 (1999).
Westphal et al., "Reactions with pyridinium pyruvic acid esters," Pharmazie, 31(11): 770-773 (1976).
English Translation of: Westphal et al., Pharmazie, 31(11): 770-773 (1976).
Wolkenberg et al., Design, Synthesis, and Evaluation of Novel 3,6 Diaryl-4-aminoalkoxyquinolones as Selective Agonists of Somatostatin Receptor Subtype 2, J Med. Chem. 54:2351-2358 (2011).
Sparrow et al., "Phospholipid meets all-trans-retinal: the making of RPE bisretinoids," J. Lipid Res.51(2):247-61 Epub Aug. 7, 2009.
U.S. Appl. No. 14/653,771.
U.S. Appl. No. 14/760,039.
International Search Report for International Application No. PCT/US2013/012356, dated May 30, 2014.
International Preliminary Report on Patentability for International Application No. PCT/US2013/012356, dated Jul. 28, 2018.
Radu et al., "Isotretinoin treatment inhibits lipofuscin accumulation in a mouse model of recessive Stargardt's macular degeneration," Novartis Foundation Symposium 25:51-63 (2004) (Abstract Only).
Yarnell, A., "Light flips the lipid switch," C&EN, 82(29):22-23 (2004).
Rizzo et al., "Ichthyosis in Sjögren-Larsson syndrome reflects defective barrier function due to abnormal lamellar body structure and secretion," Arch Dermatol Res, (2010) vol. 302, pp. 443-451.
Sciuto et al., "Therapeutic Treatments of Phosgene-Induced Lung Injury," Inhalation Toxicology, (2004) vol. 16, pp. 565-580.

* cited by examiner

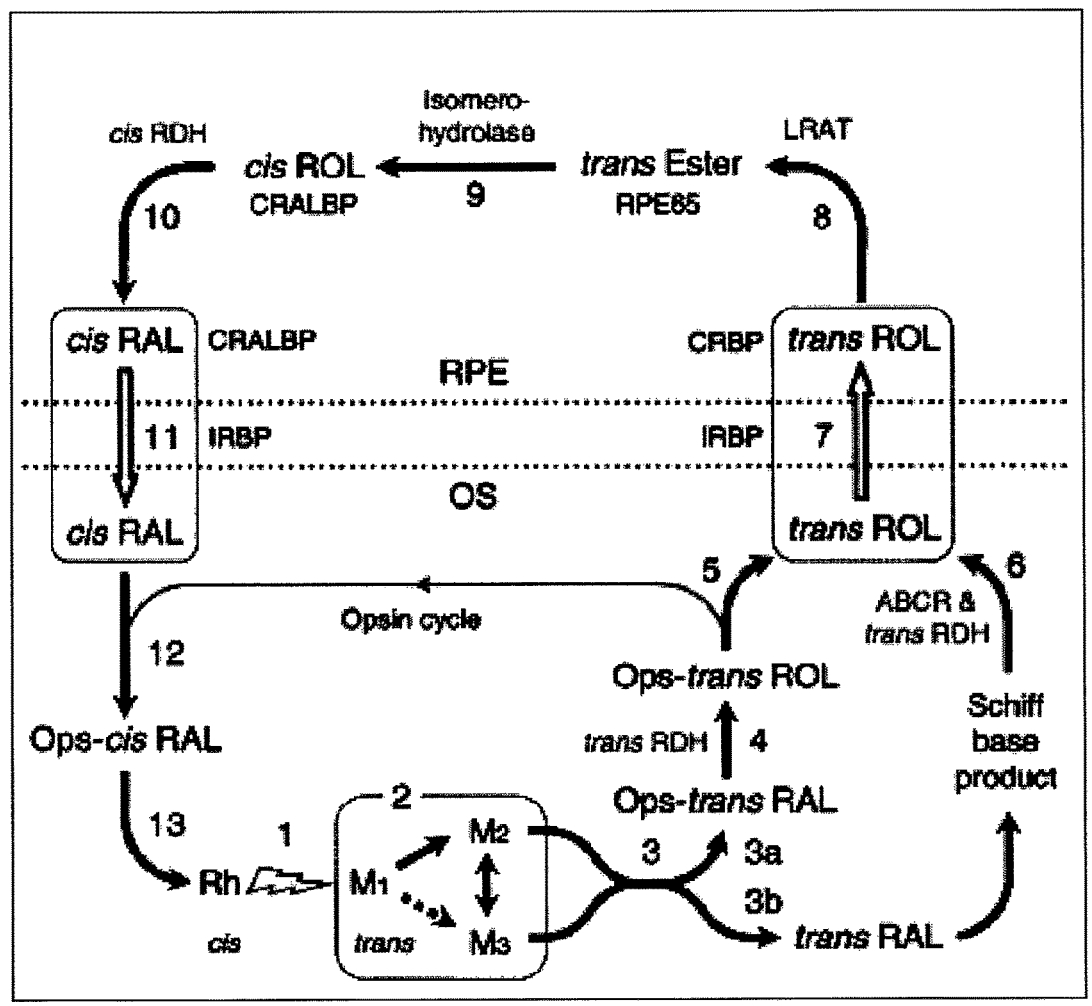

TRAPS IN THE TREATMENT OF MACULAR DEGENERATION

CROSS-REFERENCE TO RELATED APPLICATION

This application is a National Stage of International Application No. PCT/US2014/012356, filed on Jan. 21, 2014, which claims the benefit under 35 U.S.C. § 119(e) of U.S. Provisional Application No. 61/756,778, filed on Jan. 25, 2013, the contents of which are incorporated herein in their entirety.

BACKGROUND OF THE INVENTION

Macular degeneration is a leading cause of progressive blindness. The macula is the central region of the retina and contains the fovea where high acuity central vision is processed. Macular degeneration is a neurodegenerative disease in the macula that progressively causes disabling deficits in central vision which is processed by foveal cone photoreceptors, in night vision which is processed by rod photoreceptors, and in dark adaptation under conditions of both daylight (cones) and darkness (rods).

There are multiple forms of macular degeneration. Dry age-related macular degeneration (AMD) is the initial and most common form and first appears at middle age or later. Its clinical signs include an increase in fundus auto-fluorescence (FAF) and the formation of extracellular deposits called soft drusen, both caused by the accumulation of lipofuscin in retinal pigment epithelial (RPE) cells as discussed below. About 40% of dry AMD patients progress to an advanced form of the disease called geographic atrophy (GA), secondary to dry AMD, characterized by one or more atrophic retinal lesions caused by the localized death of RPE cells and adjacent retinal photoreceptor cells. Another 10% of dry AMD patients progress to wet AMD, characterized by neovascular growth from the choroid into the retina which disrupts retinal tissue and thereby destroys visual function. Finally, there is an early onset form of macular degeneration called Stargardt disease, which first appears in teenagers and young adults. Stargardt disease is believed to have the same etiology as dry AMD, but does not involve choroidal neovascularization as it progresses.

Multiple lines of evidence indicate that macular degeneration is caused by the gradual accumulation in RPE cells of a naturally occurring bis-retinoid compound called A2E (Sparrow J. R. et al., Phospholipid meets all-trans-retinal: the making of RPE bisretinoids, J. Lipid Res. Aug. 7, 2009). A2E is a cytotoxic product from the reaction of all-trans retinaldehyde (RAL) and phosphatidylethanolamine (PE), a membrane phospholipid found in the disc membranes of photoreceptor outer segments. The RAL that reacts with PE escapes from the visual cycle (step 3b in FIG. 1), a metabolic pathway in the back of the eye. The visual cycle (i) converts vitamin A from an alcohol (retinol) to a photoreactive aldehyde (11-cis-retinaldehyde) for use in phototransduction by opsin proteins in photoreceptor cell outer segments, and (ii) converts RAL to retinol after photo-transduction. As RAL escapes the visual cycle, A2E precursors form reversibly in photoreceptor outer segments, which are ingested by neighboring RPE cells after diurnal shedding. The final and irreversible step in the biosynthesis of A2E takes place in the acidic environment of RPE cell lysosomes.

As A2E accumulates in RPE cells, it gradually poisons them by multiple mechanisms including lysosomal failure and oxidative stress. Lysosomal failure leads to the accumulation of undigested cellular debris called lipofuscin, which contains A2E and can be detected clinically by FAF imaging. Oxidative stress leads to RPE cell death by apoptotic mechanisms in GA, and triggers VEGF signaling by RPE cells which causes the choroidal neovascular growth that is the hallmark of wet AMD. Complement cascades are activated by oxidized A2E in drusen and cause further pathology by inflammatory pathways. As RPE cells deteriorate, they lose their ability to participate in the visual cycle and are unable to provide photoreceptors with the metabolic support required for normal visual function. As this metabolic support is withdrawn, photoreceptors fail to renew their shed outer segments and visual function is progressively lost. By reducing the formation of A2E pharmacologically, RPE cells can recover from A2E toxicities and resume their normal metabolic support of photoreceptor cells.

The PCT publication WO 2006/127945 discloses compounds and compositions that have been shown to reduce the formation of A2E. Those compounds are designed to inhibit A2E biosynthesis by reducing the amount of free RAL available for reaction with PE in photoreceptor outer segments. However, there still exists a need for compounds with desirable properties, such as improved potency and/or pharmacological half-life. The present application addresses that need.

SUMMARY OF THE INVENTION

The invention relates to compounds, pharmaceutical compositions and methods for treating, reducing a symptom of or reducing the risk of developing a retinal disease or disorder in which the accumulation of A2E and/or lipofuscin in retinal tissue or VEGF signaling by RPE cells in response to oxidative stress is involved.

The invention relates to a compound of formula (A):

or a pharmaceutically acceptable salt thereof, wherein each of R', A', $R_1$, $R_2$, T, and n are defined herein below.

The invention also relates to a pharmaceutical composition comprising a compound of each of the formulae described herein or a pharmaceutically acceptable salt thereof, and a pharmaceutically acceptable excipient or carrier.

The invention also relates to a method of treating, reducing a symptom of or reducing the risk of developing a retinal disease or disorder in which accumulation of A2E and/or lipofuscin in retinal tissue or VEGF signaling by RPE cells in response to oxidative stress is involved.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the invention. In addition, the materials, methods, and examples are illustrative only and are not intended to be limiting.

Other features and advantages of the invention will be apparent from the following detailed description and claims.

BRIEF DESCRIPTION OF THE DRAWING

FIG. 1 is a scheme showing the visual cycle.

DETAILED DESCRIPTION OF THE INVENTION

The invention provides heteroaryl compounds of the formulae described herein. These compounds possess desirable properties, such as improved potency (e.g., more effective than various known compounds) in trapping RAL and reducing A2E formation, and/or an increased pharmacological half-life (e.g., longer than various known compounds).

In reaction with exogenous RAL in an in vitro preparation of isolated rod photoreceptor outer segments, representative compounds of this invention have more favorable reaction energetics and equilibrium constants ($K_{app}$) which are shifted toward imine and oxaminal product formation to a large extent, thus making the compounds of the invention more effective RAL traps (Table 1).

The invention relates to compounds, pharmaceutical compositions and methods for treating, reducing a symptom of or reducing the risk of developing a retinal disease or disorder in which accumulation of A2E and/or lipofuscin in retinal tissue or VEGF signaling by RPE cells in response to oxidative stress is involved. For example, the invention relates to compounds, pharmaceutical compositions and methods for treating, reducing a symptom of or reducing the risk of developing macular degeneration and other retinal diseases or disorders caused by accumulation of A2E and/or lipofuscin in retinal tissue or by VEGF signaling by RPE cells in response to oxidative stress.

In one embodiment the invention is directed to a compound of formula (A):

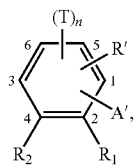
(A)

or a pharmaceutically acceptable salt thereof, wherein:

A' and R', together with the two adjacent carbon atoms to which they are attached, form a five-membered heteroaryl ring containing one nitrogen atom and one oxygen atom, wherein the heteroaryl ring is substituted with X', wherein "1", "2", "3", "4", "5", and "6" denote the points of attachment of the heteroaryl ring to the phenyl ring, provided that when the heteroaryl ring is

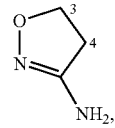

then $R_1$ is $C(D)_2OH$, $R_2$ is absent, and X' is absent, and that when the heteroaryl ring is

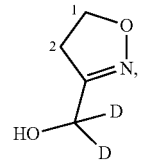

then $R_1$ is absent, $R_2$ is $NH_2$, and X' is absent;

$R_1$ is $C(D)_2OH$, or $R_1$ is absent when A' and R', together with the two adjacent carbon atoms to which they are attached, form

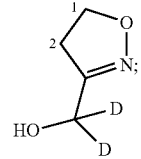

$R_2$ is $NH_2$, or $R_2$ is absent when A' and R', together with the two adjacent carbon atoms to which they are attached, form

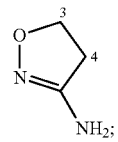

each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

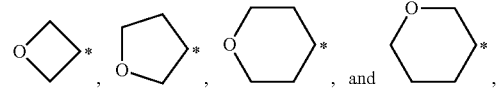

wherein "*" denotes the position of the carbon atom to which the two D are attached;

X' is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy, or X' is absent when A' and R', together with the two adjacent carbon atoms to which they are attached, form

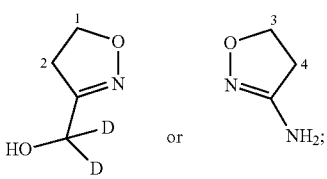 [SMILES: [2H]C([2H])(O)C1=NOCC1 ; "or" ; NC1=NOCC1]

n is 0, 1, or 2, provided that when X' is phenyl, n is not 0; and each T is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano.

In one example, A' and R', together with the two adjacent carbon atoms to which they are attached, form a five-membered heteroaryl ring containing one nitrogen atom and one oxygen atom, wherein the heteroaryl ring is substituted with X'. In one example, X' is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further example, X' is phenyl, phenyl substituted with methyl, cyclopropyl, or cyclobutyl. In another example, X' is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, X' is $C_1$-$C_6$ alkoxy (e.g., methoxy, ethoxy, and propoxy).

In one example, $R_1$ is $C(D)_2OH$ and $R_2$ is $NH_2$. In one example, each D is independently $C_1$-$C_6$ alkyl (e.g., methyl, ethyl, propyl, and butyl). In a further example, each D is methyl.

In one example, A' and R', together with the two adjacent carbon atoms to which they are attached, form

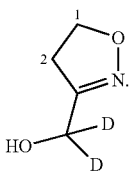

In another example, A' and R', together with the two adjacent carbon atoms to which they are attached, form

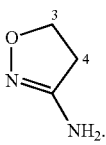

In one example, each D is independently $C_1$-$C_6$ alkyl (e.g., methyl, ethyl, propyl, and butyl). In a further example, each D is methyl.

In one example, n is 1 or 2. In a further example, n is 1.

In one example, each T is independently halogen (e.g., F, Cl, and Br). In a further example, each T is independently F or Cl. In another example, each T is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each T is independently $C_3$-$C_6$ cycloalkyl (e.g., cyclopropyl and cyclobutyl).

In one example, A' and R', together with the two adjacent carbon atoms to which they are attached, form a five-membered heteroaryl ring containing one nitrogen atom and one oxygen atom, wherein the heteroaryl ring is substituted with X'; X' is aryl, aryl substituted with methyl, or cyclopropyl; n is 1; T is Cl; $R_1$ is $C(D)_2OH$; $R_2$ is $NH_2$; and each D is methyl.

In a further example of formula (A), A' and R', together with the two adjacent carbon atoms to which they are attached, form

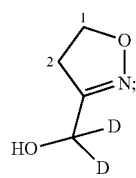

$R_2$ is $NH_2$; each D is methyl; and n is 0. In another further example of formula (A), A' and R', together with the two adjacent carbon atoms to which they are attached, form

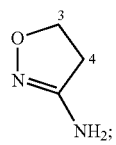

$R_1$ is $C(D)_2OH$; each D is methyl; and n is 0.

In one aspect, the compounds of formula (A) are the compounds of formula (I):

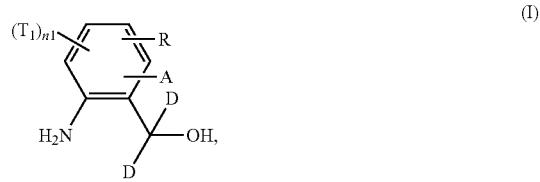

(I)

or a pharmaceutically acceptable salt thereof, wherein:

A and R, together with the two adjacent carbon atoms to which they are attached, form a five-membered heteroaryl ring containing one nitrogen atom and one oxygen atom, wherein the heteroaryl ring is substituted with X;

X is $C_1$-$C_{10}$ alkyl, $C_3$-$C_{10}$ alkyl substituted with $C_3$-$C_6$ cycloalkyl, $C_3$-$C_6$ cycloalkyl, aryl, aryl substituted with $C_3$-$C_6$ alkyl, or $C_3$-$C_6$ alkoxy;

$n_1$ is 1 or 2;

each $T_1$ is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

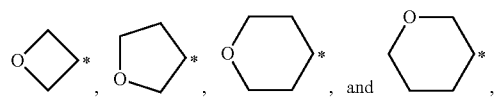

wherein "*" denotes the position of the carbon atom to which the two D are attached.

In one example, X is $C_3$-$C_6$ cycloalkyl (e.g., cyclopropyl and cyclobutyl), aryl (e.g., phenyl), or aryl (e.g., phenyl) substituted with $C_3$-$C_6$ alkyl (e.g., methyl, ethyl, propyl, and butyl). In a further example, X is phenyl, phenyl substituted with methyl, cyclopropyl, or cyclobutyl. In yet another example, X is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, X is $C_3$-$C_6$ alkoxy (e.g., methoxy, ethoxy, and propoxy).

In one example, each D is independently $C_1$-$C_6$ alkyl (e.g., methyl, ethyl, propyl, and butyl). In a further example, each D is methyl.

In one example, $n_1$ is 1.

In one example, each $T_1$ is independently halogen (e.g., F, Cl, and Br). In a further example, each $T_1$ is independently F or Cl. In another example, each $T_1$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_1$ is independently $C_3$-$C_6$ cycloalkyl (e.g., cyclopropyl and cyclobutyl).

In a further example of formula (I), X is aryl, aryl substituted with methyl, or cyclopropyl; $n_1$ is 1; $T_1$ is Cl; and each D is methyl.

One class of this aspect are the compounds of formula (Ia):

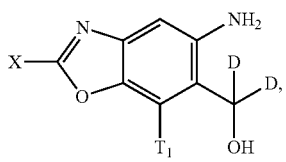

(Ia)

or a pharmaceutically acceptable salt thereof, wherein:
X is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_2$-$C_6$ alkyl, or $C_1$-$C_6$ alkoxy;
$T_1$ is F, Cl, $C_1$-$C_{10}$ alkyl, $C_1$-$C_{10}$ alkyl substituted with $C_3$-$C_6$ cycloalkyl, $C_3$-$C_6$ cycloalkyl, or cyano; and
each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

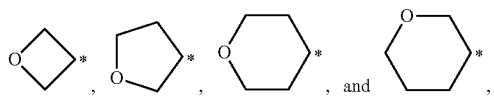

wherein "*" denotes the position of the carbon atom to which the two D are attached.

In one example, X is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further embodiment, X is phenyl, phenyl substituted with methyl, cyclopropyl, or cyclobutyl. In a further embodiment, X is phenyl or phenyl substituted with methyl. In another example, X is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, X is $C_1$-$C_6$ alkoxy (e.g., methoxy, ethoxy, and propoxy).

In one example, each D is independently $C_1$-$C_6$ alkyl (e.g., methyl, ethyl, propyl, and butyl). In a further example, each D is methyl.

In one example, $T_1$ is Cl. In another example, $T_1$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $T_1$ is independently $C_3$-$C_6$ cycloalkyl (e.g., cyclopropyl and cyclobutyl).

In a further example of formula (Ia), X is aryl or aryl substituted with methyl; $T_1$ is Cl; and each D is methyl.

Further defining the compounds of formula (Ia) are the compounds wherein:
X is $C_3$-$C_6$ cycloalkyl, aryl, or aryl substituted with $C_1$-$C_6$ alkyl;
$T_1$ is F, Cl, methyl, cyclopropyl, cyclobutyl, or cyano; and
each D is independently $C_1$-$C_6$ alkyl or $C_3$-$C_6$ cycloalkyl,
or a pharmaceutically acceptable salt thereof.

In one subclass are the compounds wherein:
$T_1$ is F, Cl, methyl, or cyano; and
D is methyl,
or a pharmaceutically acceptable salt thereof.

Further illustrating the compounds of formula (Ia) are compounds 2 and 3:

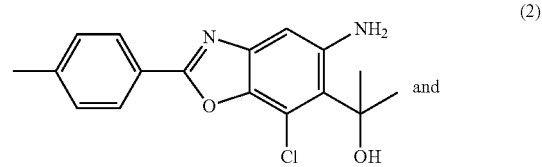

(2)

and

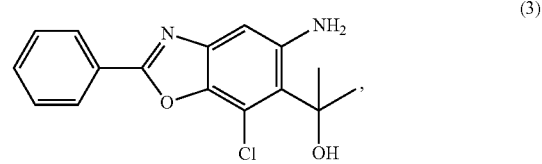

(3)

or a pharmaceutically acceptable salt thereof.

Another class of this aspect are the compounds of formula (Ib) or (Ic):

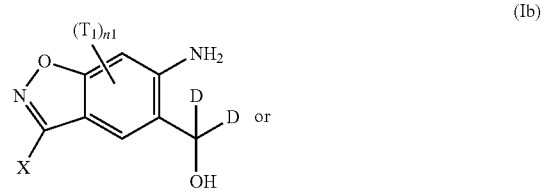

(Ib)

or

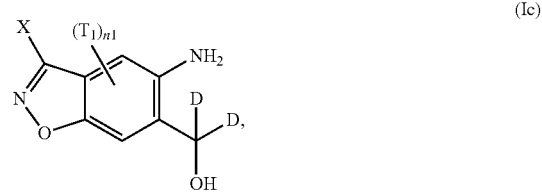

(Ic)

or a pharmaceutically acceptable salt thereof, wherein:
X is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;
$n_1$ is 1 or 2;

each $T_1$ is independently F, Cl, $C_1$-$C_{10}$ alkyl, $C_1$-$C_{10}$ alkyl substituted with $C_3$-$C_6$ cycloalkyl, $C_3$-$C_6$ cycloalkyl, or cyano; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

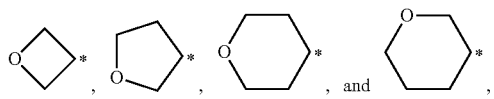

wherein "*" denotes the position of the carbon atom to which the two D are attached.

In one example, X is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further embodiment, X is phenyl, phenyl substituted with methyl, cyclopropyl, or cyclobutyl. In a further embodiment, X is cyclopropyl or cyclobutyl. In another example, X is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, X is $C_1$-$C_6$ alkoxy (e.g., methoxy, ethoxy, and propoxy).

In one example, each D is independently $C_1$-$C_6$ alkyl (e.g., methyl, ethyl, propyl, and butyl). In a further example, each D is methyl.

In one example, $n_1$ is 1.

In one example, each $T_1$ is Cl. In another example, each $T_1$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_1$ is independently $C_3$-$C_6$ cycloalkyl (e.g., cyclopropyl and cyclobutyl).

In a further example of formula (Ib) or (Ic), X is cyclopropyl; $n_1$ is 1; $T_1$ is Cl; and each D is methyl.

Further defining the compounds of formulae (Ib) and (Ic) are the compounds wherein:

X is $C_3$-$C_6$ cycloalkyl, aryl, or aryl substituted with $C_1$-$C_6$ alkyl;

$n_1$ is 1;

$T_1$ is F, Cl, methyl, cyclopropyl, cyclobutyl, or cyano; and each D is independently $C_1$-$C_6$ alkyl or $C_1$-$C_6$ cycloalkyl, or a pharmaceutically acceptable salt thereof.

Further illustrating the compounds of formula (Ib) or (Ic) are the compounds of formula (Ib-1) or (Ic-1):

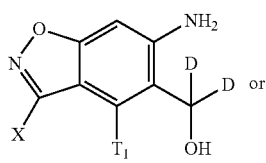

(Ib-1)

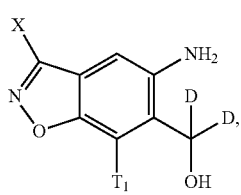

(Ic-1)

or a pharmaceutically acceptable salt thereof, wherein X, $T_1$, and D are defined above in formula (Ib) or (Ic).

Further defining the compounds of formula (Ib-1) or (Ic-1) are the compounds wherein:

X is $C_3$-$C_6$ cycloalkyl, aryl, or aryl substituted with $C_1$-$C_6$ alkyl;

$T_1$ is F, Cl, methyl, cyclobutyl, cyclopropyl, or cyano; and each D is independently $C_1$-$C_6$ alkyl or $C_1$-$C_6$ cycloalkyl, or a pharmaceutically acceptable salt thereof.

For example, X is cyclopropyl or cyclobutyl; $T_1$ is F or Cl; and each D is independently $C_1$-$C_6$ alkyl.

Further illustrating the compounds of formula (Ib) or (Ic) are compounds 4 and 5:

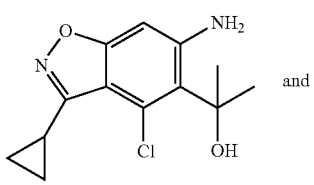

(4)

and

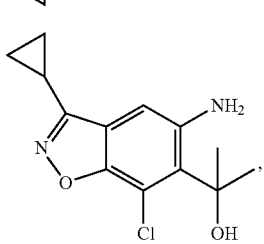

(5)

or a pharmaceutically acceptable salt thereof.

A third class of this aspect are the compounds of formula (Id):

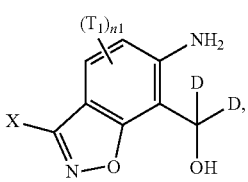

(Id)

or a pharmaceutically acceptable salt thereof, wherein:

X is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;

$n_1$ is 1 or 2;

each $T_1$ is independently F, Cl, $C_1$-$C_{10}$ alkyl, $C_3$-$C_6$ cycloalkyl, $C_1$-$C_{10}$ alkyl substituted with $C_3$-$C_6$ cycloalkyl, or cyano; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

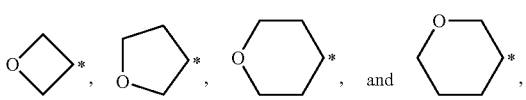

wherein "*s" denotes the position of the carbon atom to which the two D are attached.

In one example, X is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further embodiment, X is phenyl, phenyl substituted with methyl, cyclopropyl, or cyclobutyl. In a further embodiment, X is cyclopropyl or cyclobutyl. In another example, X is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, X is $C_1$-$C_6$ alkoxy (e.g., methoxy, ethoxy, and propoxy).

In one example, each D is independently $C_1$-$C_6$ alkyl (e.g., methyl, ethyl, propyl, and butyl). In a further example, each D is methyl.

In one example, $n_1$ is 1.

In one example, each $T_1$ is Cl. In another example, each $T_1$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_1$ is independently $C_3$-$C_6$ cycloalkyl (e.g., cyclopropyl and cyclobutyl).

In a further example of formula (Id), X is cyclopropyl; $n_1$ is 1; $T_1$ is Cl; and each D is methyl.

Further defining the compounds of formula (Id) are the compounds wherein:

X is $C_3$-$C_6$ cycloalkyl, aryl, or aryl substituted with $C_1$-$C_6$ alkyl;

$n_1$ is 1;

$T_1$ is F, Cl, methyl, cyclopropyl, cyclobutyl, or cyano; and each D is independently $C_1$-$C_6$ alkyl or $C_1$-$C_6$ cycloalkyl, or a pharmaceutically acceptable salt thereof.

Further illustrating this class is compound 6:

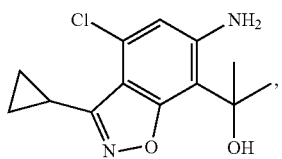

(6)

or a pharmaceutically acceptable salt thereof.

In a second aspect, the compounds of formula (A) are the compounds of formula (II):

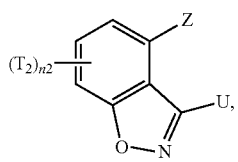

(II)

or a pharmaceutically acceptable salt thereof, wherein:

one of U and Z is $C(D)_2OH$, and the other is $NH_2$;

each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

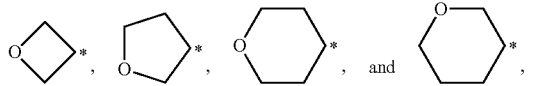

wherein "*" denotes the position of the carbon atom to which the two D are attached;

$n_2$ is 0, 1, or 2; and each $T_2$ is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano.

In one example, each D is independently $C_1$-$C_6$ alkyl (e.g., methyl, ethyl, propyl, and butyl). In a further example, each D is methyl.

In one example, $n_2$ is 0 or 1. In a further example, $n_2$ is 0.

In one example, each $T_2$ is independently halogen (e.g., F, Cl, and Br). In a further example, each $T_2$ is independently F or Cl. In another example, each $T_2$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_2$ is independently $C_3$-$C_6$ cycloalkyl (e.g., cyclopropyl and cyclobutyl).

In a further example of formula (II), $n_2$ is 0; and each D is methyl.

One class of this aspect are the compounds of formula (IIa) or (IIb):

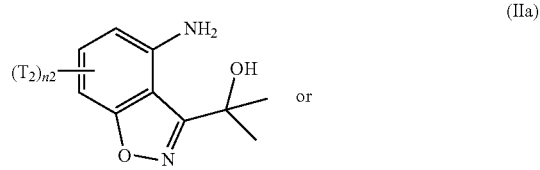

(IIa)

or

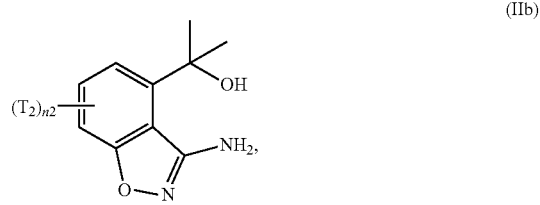

(IIb)

or a pharmaceutically acceptable salt thereof, wherein:

$n_2$ is 0, 1, or 2; and each $T_2$ is independently F, Cl, $C_1$-$C_{10}$ alkyl, $C_1$-$C_{10}$ alkyl substituted with $C_3$-$C_6$ cycloalkyl, $C_3$-$C_6$ cycloalkyl, or cyano.

In one example, $n_2$ is 0 or 1. In a further example, $n_2$ is 0.

In one example, each $T_2$ is Cl. In another example, each $T_2$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_2$ is independently $C_3$-$C_6$ cycloalkyl (e.g., cyclopropyl and cyclobutyl).

Further illustrating the compounds of formula (IIa) or (IIb) are compounds 7 and 8:

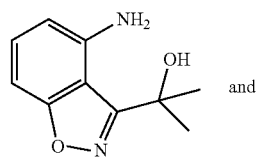

(7)

and

-continued

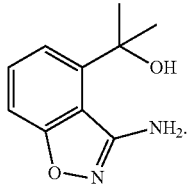

(8)

Representative compounds of the invention include compounds listed in the table below.

| Compound No. | Chemical Structure |
|---|---|
| 2 | (structure: 2-(4-methylphenyl)benzoxazole with NH₂, Cl, and C(CH₃)₂OH substituents) |
| 3 | (structure: 2-phenylbenzoxazole with NH₂, Cl, and C(CH₃)₂OH substituents) |
| 4 | (structure: 3-cyclopropyl-benzisoxazole with NH₂, Cl, and C(CH₃)₂OH substituents) |
| 5 | (structure: 3-cyclopropyl-benzisoxazole isomer with NH₂, Cl, and C(CH₃)₂OH substituents) |
| 6 | (structure: 3-cyclopropyl-benzisoxazole with Cl, NH₂ and C(CH₃)₂OH) |
| 7 | (structure: benzisoxazole with NH₂ and C(CH₃)₂OH) |
| 8 | (structure: benzisoxazole with OH, NH₂ and C(CH₃)₂) |

The compounds of the invention possess desirable properties. For example, the compounds of the invention have an apparent second order rate constant of RAL depletion, $k_{app}$, of at least 5,000, 10,000, 12,500, 15,000, 20,000, 25,000, 26,000, or 30,000 ($M^{-1} \cdot h^{-1}$). In a further example, the compounds of the invention have a $k_{app}$ of at least 12,500, 20,000, or 26,000 ($M^{-1} \cdot h^{-1}$). In another example, the compounds of the invention have an apparent equilibrium constant of RAL depletion, $K_{app}$, of at least $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or $2.0 \times 10^6$. In a further example, the compounds of the invention have a $K_{app}$ of at least $1.5 \times 10^6$, $1.6 \times 10^6$, $1.7 \times 10^6$, $1.8 \times 10^6$, $1.9 \times 10^6$, or $2.0 \times 10^6$. In another example, the compounds of the invention have an apparent free energy change of RAL depletion, $\Delta G_{app}$, lower than −8.7, −8.8, −8.9, −9.0, −9.1, −9.2, −9.3, −9.4, −9.5, −9.6, −9.7, −9.8, −9.9, −10.0 kcal/mol. In a further example, the compound of the invention has a $\Delta G_{app}$ lower than −8.8, −9.0, −9.1, or −9.2 kcal/mol. $k_{app}$, $K_{app}$, and $\Delta G_{app}$ can be measured by various known methods, such as those described herein.

A second embodiment of the invention is directed to a method of treating, reducing a symptom of or reducing the risk of a retinal disease or disorder in which accumulation of A2E and/or lipofuscin in retinal tissue or VEGF signaling by RPE cells in response to oxidative stress is involved. For example, the invention is directed to a method of treating, reducing a symptom of or reducing the risk of macular degeneration and other retinal diseases or disorders caused by accumulation of A2E and/or lipofuscin in retinal tissue or by VEGF signaling by RPE cells in response to oxidative stress, including dry age-related macular degeneration (AMD), geographic atrophy (GA) secondary to dry AMD, wet AMD and Stargardt disease. The method includes administering a pharmaceutical composition comprising a compound of the invention, such as a compound of formulae (A), (I), and (II), to a subject in need thereof, such as a patient having or being at a risk of developing macular degeneration or a retinal disease or disorder in which accumulation of A2E and/or lipofuscin in retinal tissue or VEGF signaling by RPE cells in response to oxidative stress is involved. Exemplifying this aspect is a method of treating, reducing a symptom of or reducing the risk of macular degeneration, dry AMD or GA secondary to dry AMD. Also exemplifying this aspect is a method of treating, reducing a symptom of or reducing the risk of wet AMD. This aspect is also exemplified by a method of treating, reducing a symptom of or reducing the risk of Stargardt disease.

In the methods of the invention, the level of A2E should be lowered relative to that in the subject (e.g., a patient) prior to the administration of a composition comprising a compound of the invention, such as a compound of formulae (A), (I), and (II). More specifically, the method comprises administering a composition wherein the compound is selected from:

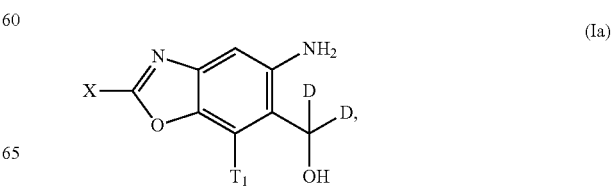

(Ia)

-continued (Ib)
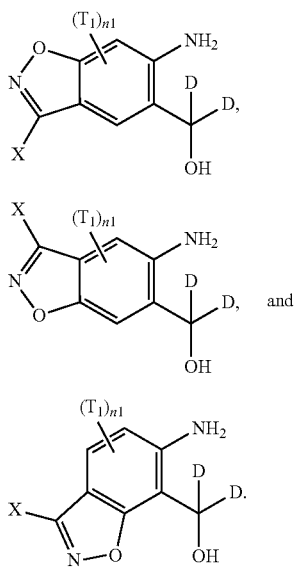
(Ic)

(Id)

or a pharmaceutically acceptable salt thereof.

The method is further illustrated by administering a composition wherein the compound is selected from:

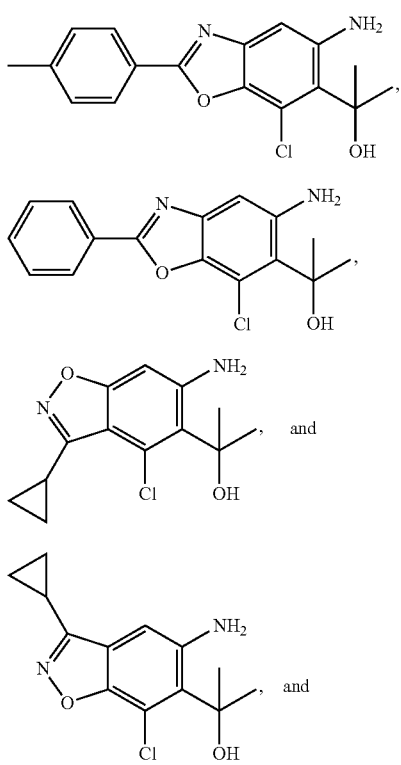

(2)

(3)

(4)

(5)

-continued (6)
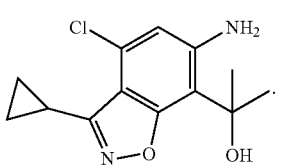

or a pharmaceutically acceptable salt thereof.

The method is yet further illustrated by administering a composition wherein the compound is selected from:

(IIa)
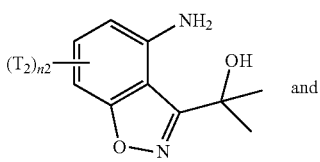

(IIb)
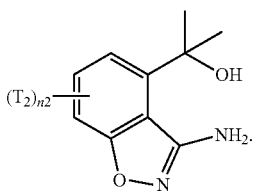

or a pharmaceutically acceptable salt thereof.

The method is further illustrated by administering a composition wherein the compound is selected from:

(7)
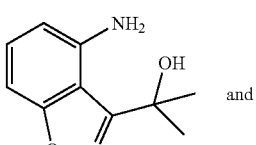

(8)
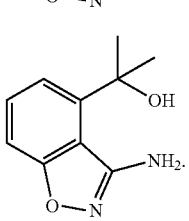

It should be understood that each form of macular degeneration may be treated in the method of the invention.

The compounds of the invention may be readily prepared by those skilled in the art. In particular the compounds of the invention may be prepared following the schemes illustrated below:

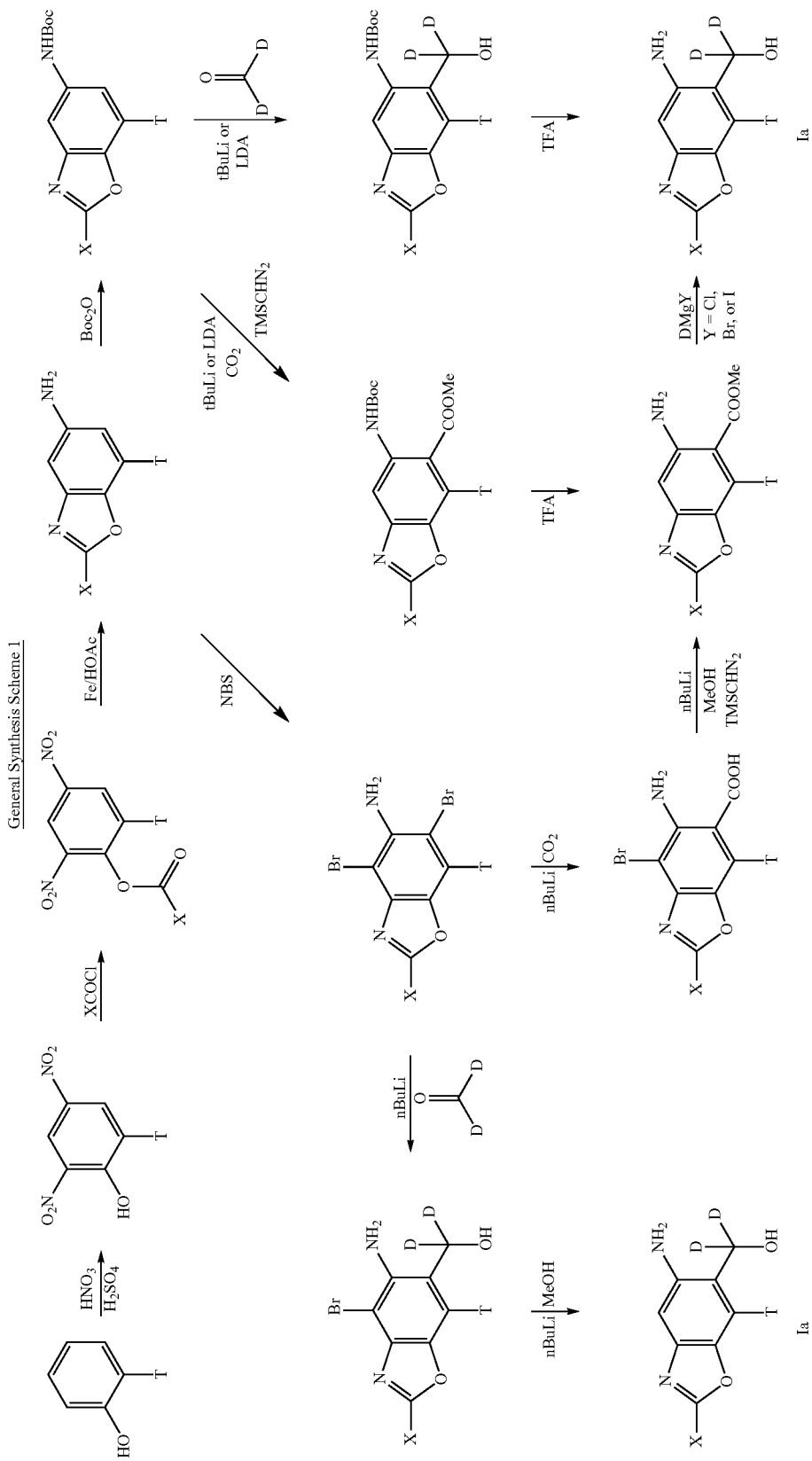

General Synthesis Scheme 2
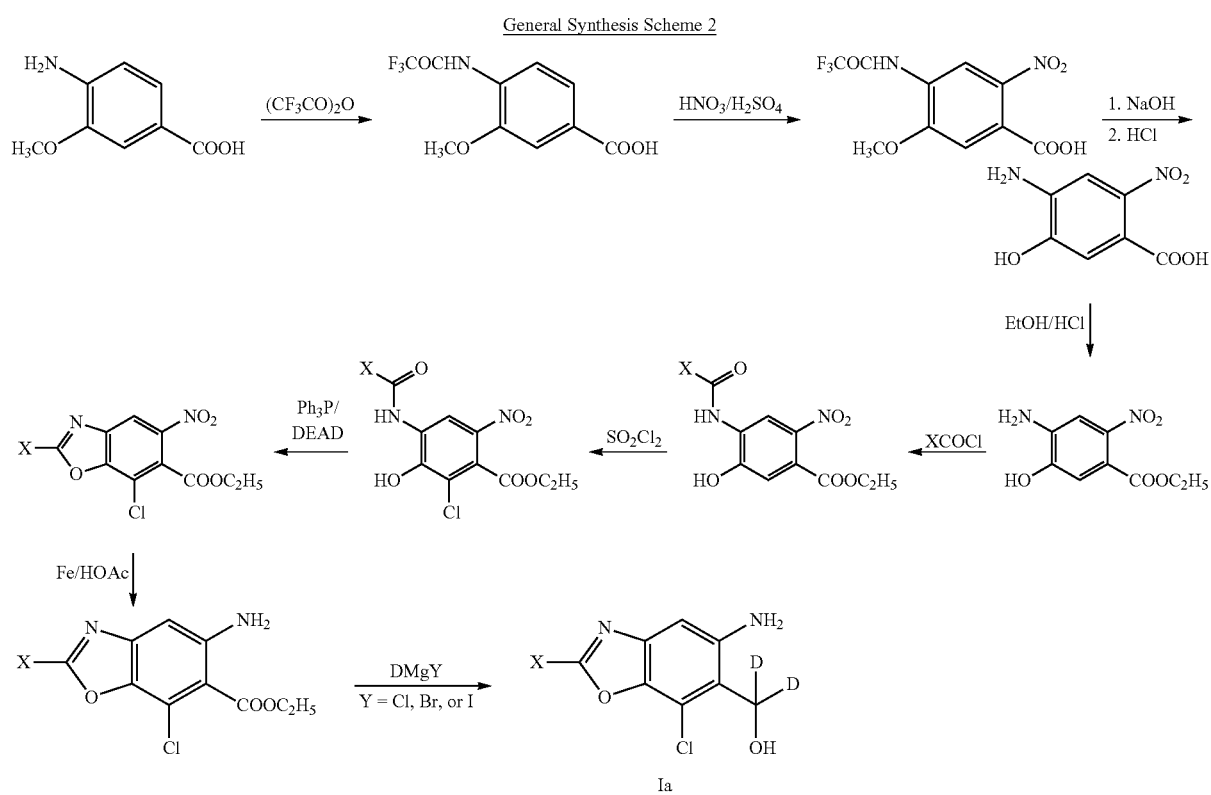
When T = Cl, compounds of the invention (e.g., formula (Ia)) can be prepared as shown in Scheme 2.
DEAD: diethyl azodicarboxylate
General Synthesis Scheme 3
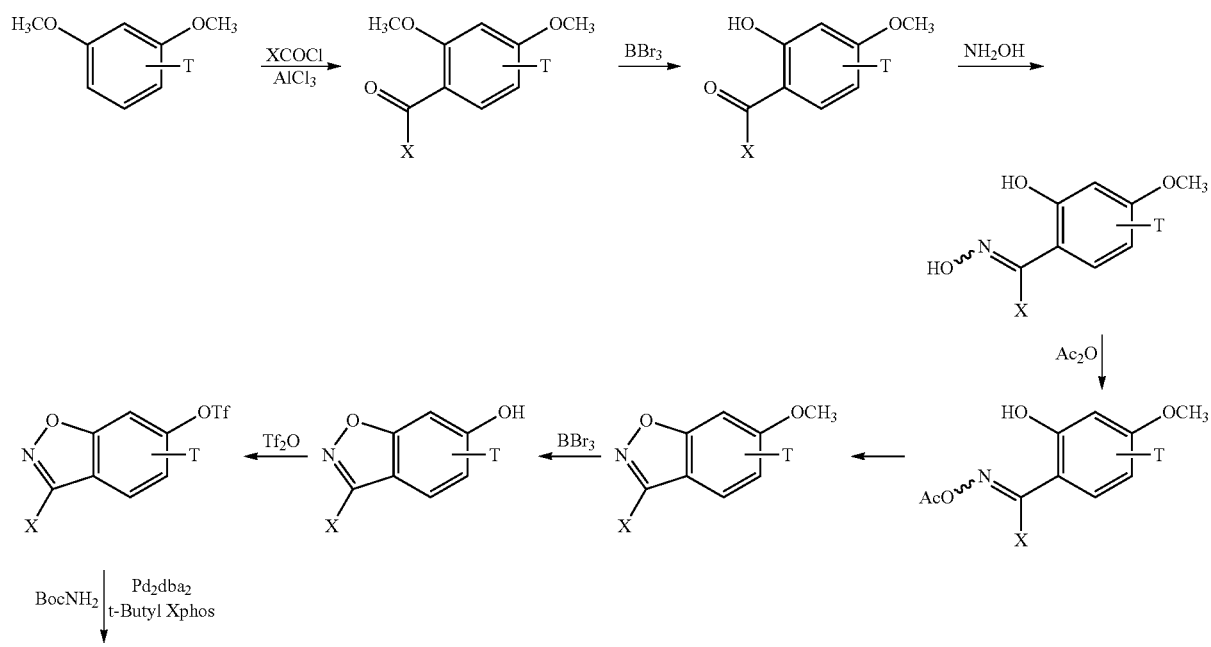

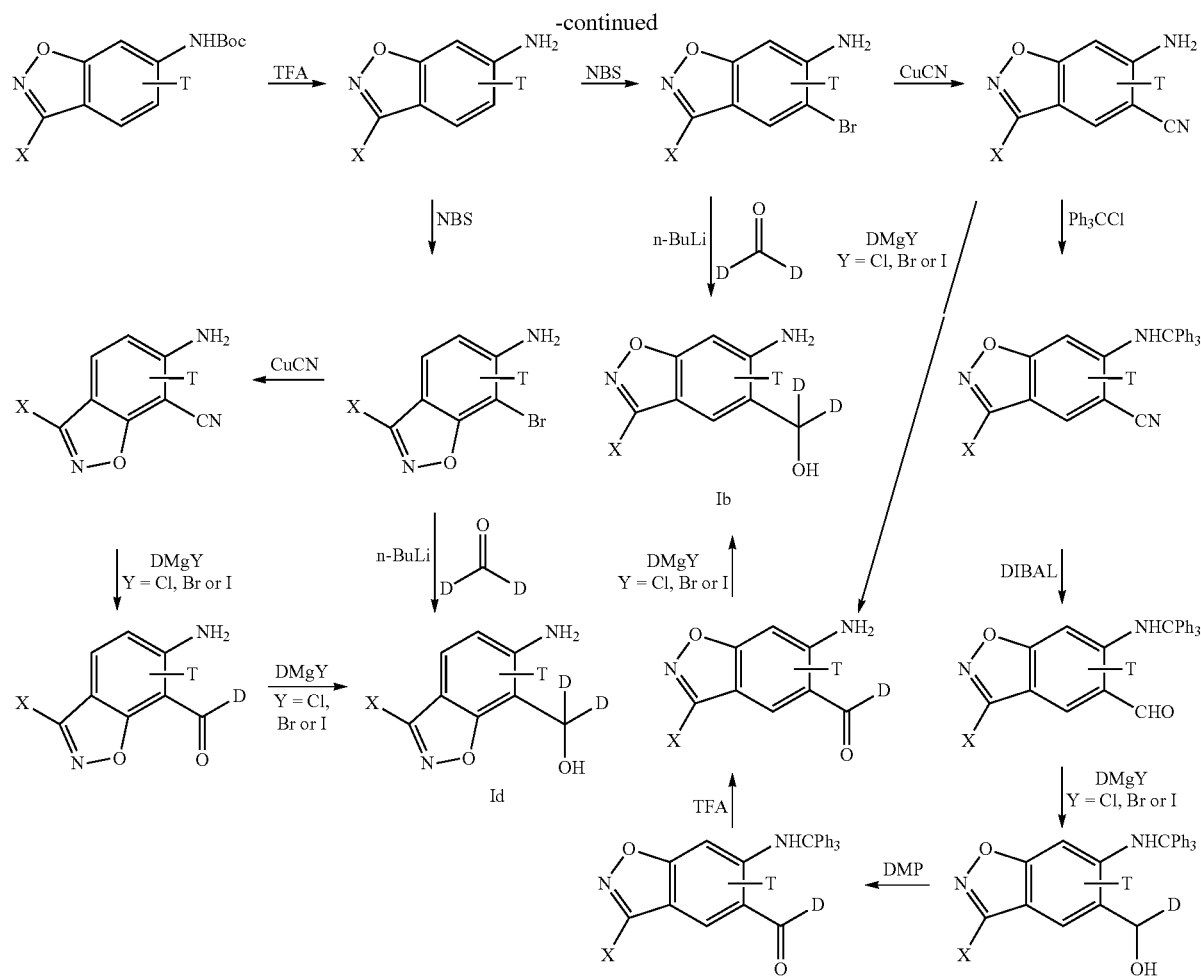
Compounds of the invention (e.g., formulae (Ib) and (Id)) can be prepared as shown in Scheme 3.
TFA: trifluoroacetic acid;
NBS: N-bromosuccinimide;
DIBAL: diisobutylaluminium hydride;
DMP: Dess-Martin periodinane
General Synthesis Scheme 4
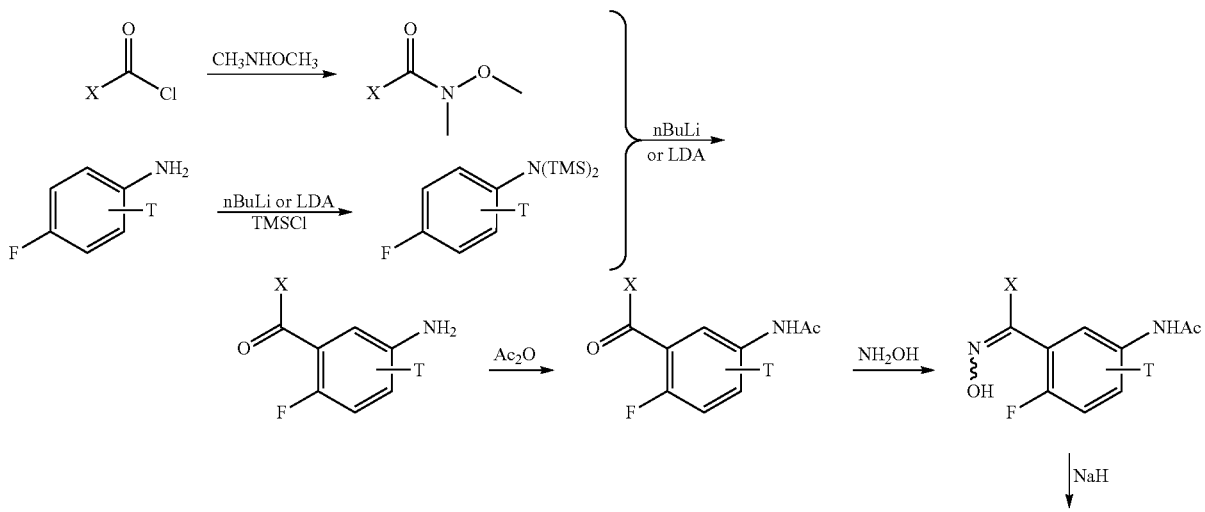

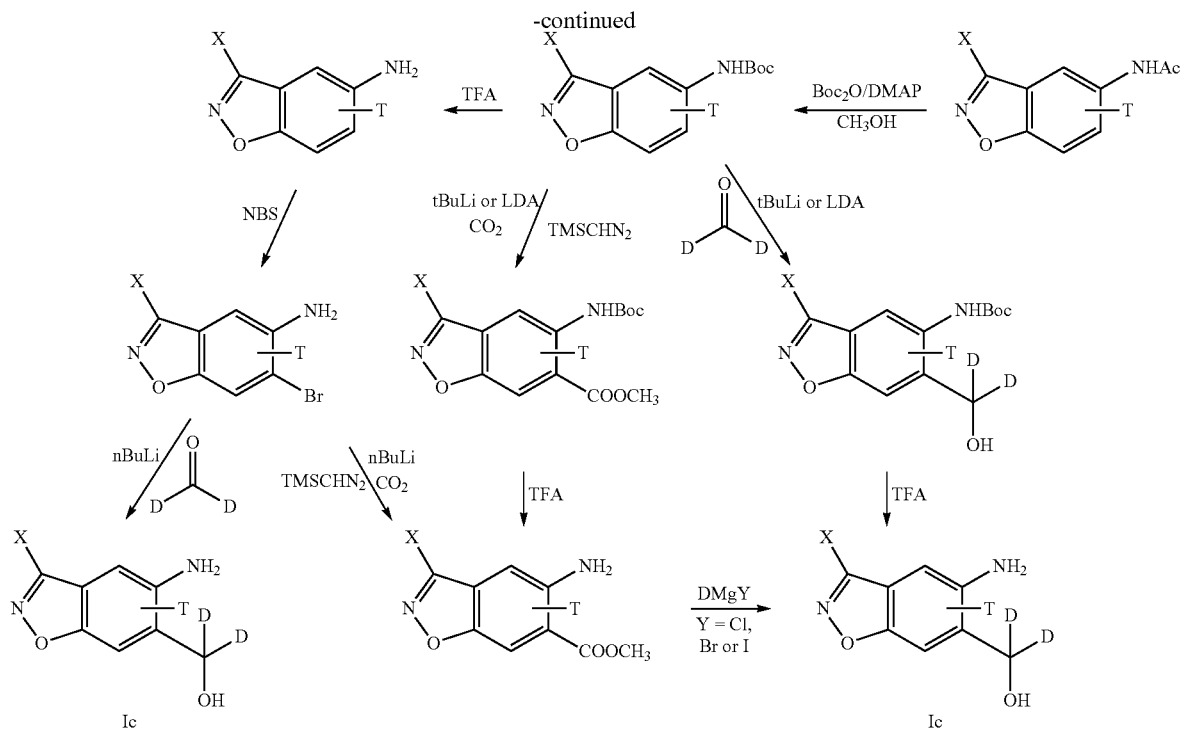

Compounds of the invention (e.g., formula (Ic)) can be prepared as shown in Scheme 4.
LDA: lithium diisopropylamide;
TMSCl: trimethylsilyl chloride;
DMAP: 4-dimethylaminopyridine;
TFA: trifluoroacetic acid;
TMSCHN$_2$: trimethylsilyldiazomethane;
NBS: N-bromosuccinimide General Synthesis Schemes 5-1 and 5-2

Compounds of the invention (e.g., formulae (IIa) and (IIb)) can be prepared as shown in Schemes 5-1 and 5-2.

Scheme 5-1:

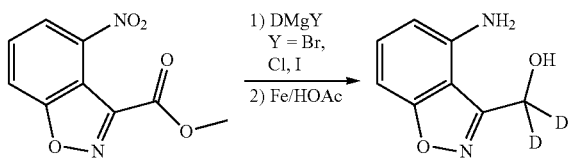

Starting material may be made by methods known in the art, such as that described in Ji Z. et al., Bioorg. & Med. Chem. Let. (2012), 22, 4528

Scheme 5-2:

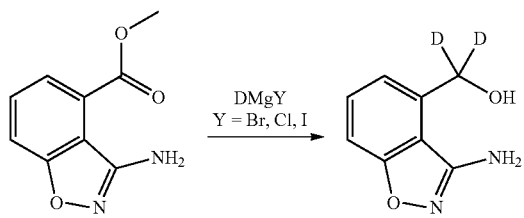

Starting material may be made by methods known in the art, such as that described in Smalley R. K., Science of Synthesis (2002), 11, 289

As used herein the following definitions are applicable.

"Alkyl" means carbon chains which may be linear or branched. $C_1$-$C_6$ alkyl includes straight chain $C_1$-$C_6$ alkyl and branched $C_3$-$C_6$ alkyl, and $C_1$-$C_{10}$ alkyl includes straight chain $C_1$-$C_{10}$ alkyl and branched $C_3$-$C_{10}$ alkyl. Examples of alkyl groups include methyl, ethyl, n-propyl, isopropyl, n-, iso-, sec- and tert-butyl, pentyl, hexyl and the like. When alkyl is methyl, it should be understood that deuteromethyl is also included within the definition of methyl and the scope of the invention.

"Cycloalkyl", "carbocycle", or "carbocyclic" means a saturated carbocyclic ring having a specified number of carbon atoms, e.g. $C_3$-$C_6$ cycloalkyl is a ring containing 3, 4, 5, or 6 carbon atoms, including cyclopropyl, cyclobutyl, cyclopentyl and cyclohexyl.

"Halogen" includes fluorine, chlorine, bromine and iodine.

"Aryl" means an aromatic moiety such as phenyl, naphthyl, and tolyl.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

The term "alkoxy" or "alkoxyl" includes substituted and unsubstituted alkyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups.

Compounds within the scope of the instant invention may contain chiral centers and thus are capable of existing as racemates, racemic mixtures, diastereomers and single enantiomers. All such forms should be understood as within the scope of this invention.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

The term "pharmaceutically acceptable salts" is art-recognized, and includes relatively non-toxic, inorganic and organic acid addition salts of compositions, including without limitation, the compounds of the invention, excipients, carriers and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci. 66:1-19 (1977).

The compounds of the instant invention may be administered in the parent form or as a pharmaceutically acceptable salt. The term compound of the invention should be understood to include both. Pharmaceutically acceptable salts can be prepared from a parent compound that contains basic or acidic moieties by conventional chemical methods. Acid addition salts would include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 4,4'-methylenebis(3-hydroxy-2-naphthoate]) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For reviews on pharmaceutically acceptable salts see S. M. Berge, L. D. Bighley and D. C. Monkhouse, Pharmaceutical Salts, *J. Pharm. Sci.,* 66 (1977), 1-19 and P. H. Stahl and C. G. Wermuth (eds.), *Pharmaceutical Salts: Properties, Selection, and Use,* Weinheim, Germany: Wiley and Zürich: Verlag Helvetica Chimica Acta, 2002 [ISBN 3-906390-26-8], incorporated herein by reference. Reference to the parent compound or a salt thereof should be understood to include all hydrates and solvates of the compound and all polymorphic forms of the parent compound.

A "patient," "subject," or "host" to be treated by the subject method may mean either a human or non-human animal, such as primates, mammals, and vertebrates.

The present invention provides compounds, compositions and methods for treating, reducing a symptom of and reducing the risk of a retinal disease or disorder in which accumulation of A2E and/or lipofuscin in retinal tissue or VEGF signaling by RPE cells in response to oxidative stress is involved. For examples, the present invention provides compounds, compositions and methods for treating, reducing a symptom of and reducing the risk of macular degeneration or other retinal diseases or disorders caused by accumulation of A2E and/or lipofuscin in retinal tissue or by VEGF signaling by RPE cells in response to oxidative stress. Specifically the compounds are useful in treating all forms of macular degeneration, including dry AMD, GA secondary to dry AMD, wet AMD and Stargardt disease. Multiple lines of evidence indicate that the fundamental cause of all such forms of the disease is the cytotoxicity that results from the accumulation of A2E and lipofuscin inside RPE cells which causes lysosomal failure and oxidative stress. This in turn triggers the apoptosis of GA, VEGF signaling in RPE cells, which leads to the choroidal neovascularization of wet AMD and the formation of drusen whose A2E-oxirane derivatives trigger complement activation. A2E synthesis and accumulation can be reduced pharmacologically, which in turn treats or lowers the risk of macular degeneration including dry AMD and other forms of macular degeneration, by limiting the amount of RAL available for reaction with PE which is the first step in the A2E biosynthetic pathway, and the progression from dry AMD to GA and wet AMD. In the PCT publication WO 2006/127945, compounds are described which reduce RAL concentrations in photoreceptor outer segments by chemically reacting irreversibly with RAL and thus are useful in treating or lowering the risk of macular degeneration in a patient. The compounds of the instant invention are more potent than those described in WO 2006/127945 and may show a decreased susceptibility to metabolic oxidation as well as improved pharmacokinetics and pharmacodynamics in vivo.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease, disorder or condition includes ameliorating at least one symptom of the particular disease, disorder or condition, even if the underlying pathophysiology is not affected.

The term "preventing" is art-recognized and includes stopping a disease, disorder or condition from occurring in a subject which may be predisposed to the disease, disorder and/or condition but has not yet been diagnosed as having it. Preventing a condition related to a disease includes stopping the condition from occurring after the disease has been diagnosed but before the condition has been diagnosed.

The term "reducing the risk of" means that the likelihood of a subject to suffer from a disease, disorder or condition is decreased, for example, from between 50% and 100% to between 0 and 90%, between 0 and 80%, between 0 and 70%, between 0 and 60%, or between 0 and 50%, or decreased by 10%, 20%, 30%, 40%, 50%, 60%, 70%, 80%, or 90%.

The present invention is also directed to the manufacture of a medicament for treating, reducing a symptom of or reducing the risk of developing a retinal disease or disorder in which accumulation of A2E and/or lipofuscin in retinal tissue or VEGF signaling by RPE cells in response to oxidative stress is involved in a subject in need thereof; wherein the composition comprises a compound of the invention or a pharmaceutically acceptable salt thereof. In one illustration, the present invention is directed to a method for the manufacture of a medicament for the treatment, reduction of a symptom of or reduction of risk of macular degeneration in a patient. More specifically, this aspect of the invention is directed to the manufacture of a medicament for the treatment or reduction of risk of macular degeneration disease in a patient, including dry AMD, GA secondary to dry AMD, wet AMD and Stargardt disease.

The present invention is also directed to a composition for use in a method for treating, reducing a symptom of or reducing the risk of developing a retinal disease or disorder in which accumulation of A2E and/or lipofuscin in retinal tissue or VEGF signaling by RPE cells in response to oxidative stress is involved in a subject in need thereof, wherein the composition comprises a compound of the invention or a pharmaceutically acceptable salt thereof. In one illustration, the invention is directed to a composition for use in a method for treating, reducing a symptom of or reducing the risk of developing macular degeneration. More specifically, this aspect of the invention is directed to a composition for use in a method for treating, reducing a symptom of or reducing the risk of developing macular degeneration in a patient, including dry AMD, GA secondary to dry AMD, wet AMD and Stargardt disease.

The compounds of the invention may be administered with a pharmaceutically acceptable carrier in a pharmaceutical composition. The pharmaceutical compositions of the present invention encompass any composition made by admixing a therapeutically effective amount of a compound of the invention with a pharmaceutically acceptable carrier. The administration may be by oral, parenteral, topical or intra-ocular means. Topical administration may be in the form of drops or controlled release topical formulations including films and adhesives. Intra-ocular administration may take the form of subconjunctival, sub-Tenon, retrobulbar or intravitreal injections, depots or implants. Compounds administered by these routes may be in solution or suspension form. Administration of compounds by depot injection may contain pharmaceutically acceptable carriers or excipients, which may be natural or synthetic and biodegradable or non-biodegradable and may facilitate drug release in a controlled manner. Implants used for controlled release of compound may be composed of natural or synthetic, biodegradable or non-biodegradable materials. The carrier is acceptable in that it is compatible with the other components of the composition and is not injurious to the patient. Some examples of carriers include (1) sugars such as lactose glucose and sucrose, (2) starches such as corn starch and potato starch, (3) cellulose and (4) cyclodextrins. A useful topical formulation is described in the PCT publication WO 2011/072141, the contents of which are herein incorporated by reference.

In one exemplification, the pharmaceutical compositions of the present invention encompass a composition made by admixing a therapeutically effective amount of a compound of the invention with an oligomeric or a polymeric carrier such as a cyclodextrin, or chemically modified cyclodextrin, including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt). Exemplifying an oligomeric or a polymeric carrier is β-cyclodextrin sulfobutylether sodium salt. The amount of β-cyclodextrin sulfobutylether sodium salt in the composition may range from about 0.01% to 30% weight/volume. In one illustration, the concentration of β-cyclodextrin sulfobutylether sodium salt is 5-25% weight/volume. Further illustrating the concentration of β-cyclodextrin sulfobutylether sodium salt is 6-20% weight/volume. In one exemplification the concentration of β-cyclodextrin sulfobutylether is 6-12% weight/volume. Further exemplifying the concentration of β-cyclodextrin sulfobutylether is 9-10% weight/volume, including 9.5% weight/volume. The amount of the compound of the invention in the composition may range 0.01-20%, 0.02-15%, 0.04-10%, 0.06-5%, 0.08-1%, or 0.09-0.5% (weight/volume). More particularly, the composition may contain a compound of the invention at a concentration of 0.09-0.5% (weight/volume), such as 0.1%. Efficacious levels of the composition comprising a compound of the invention and a cyclodextrin can be delivered to the back of the eye and specifically to the RPE and retina. The composition may further comprise saline and may be buffered with, for example, a phosphate buffer, so that the pH of the composition is brought to a pH range of 5.5-8.5 or, more particularly, a pH range of 6.5-7.5. A preservative may optionally be included in the composition. Such preservatives can include both chemical stabilizers, such as an anti-oxidant, and antiseptics.

In an eye drop formulation the composition may contain the active compound at a concentration of 0.01-20%, 0.02-15%, 0.04-10%, 0.06-5%, 0.08-1%, or 0.09-0.5% (weight/volume). More particularly, the eye drop formulation contains a compound of the invention at a concentration of 0.09-0.5% (weight/volume), such as 0.1%.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. A therapeutically effective dose, of a compound of the invention in an oral formulation, may vary from 0.01 mg/kg to 50 mg/kg patient body weight per day, more particularly 0.01 to 10 mg/kg, which can be administered in single or multiple doses per day. For oral administration the drug can be delivered in the form of tablets or capsules containing 1 mg to 500 mg of the active ingredient specifically, 1 mg, 5 mg, 10 mg, 20 mg, 50 mg, 100 mg, 250 mg, and 500 mg, or in the form of tablets or capsules containing at least 1%, 2%, 5%, 10%, 15%, 20%, 25%, 30%, 40%, 50% (w/w) of the active ingredient. For example, the capsules may contain 50 mg of the active ingredient, or 5-10% (w/w) of the active ingredient. For example, the tablets may contain 100 mg of the active ingredient, or 20-50% (w/w) of the active ingredient. For example, the tablet may contain, in addition to the active ingredient, a disintegrant (e.g., croscarmellose or its sodium salt and methyl cellulose), a diluent (e.g., microcrystalline cellulose), and a lubricant (e.g., sodium stearate and magnesium stearate). The drug can be administered on a daily basis either once, twice or more per day.

Parenteral formulations comprising a compound of the invention can be prepared in aqueous isotonic solutions or suspensions, and suppositories are advantageously prepared from fatty emulsions or suspensions. The formulations may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional methods, and may contain about 0.1 to 75%, preferably about 1 to 50%, of a compound of the invention.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

A "pharmaceutical composition" is a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, parenteral, topical, intra-ocular, and the like. Dosage forms for topical administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and optionally with any preservatives, buffers, or propellants that may be required.

The compounds of the invention are provided in therapeutic compositions. The compound is present in an amount that is therapeutically effective, which varies widely depending largely on the particular compound being used. The preparation of pharmaceutical or pharmacological compositions will be known to those of skill in the art in light of the present disclosure.

The terms "administering of" or "administering a" should be understood to mean providing a compound of the invention or a prodrug thereof to a patient in need of treatment or reduction in risk.

Upon formulation, therapeutics will be administered in a manner compatible with the dosage formulation, and in such amount as is pharmacologically effective. The formulations are easily administered in a variety of dosage forms, such as the forms described above.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. The amount of compound incorporated into the composition also depends upon the desired release profile, the concentration of the compound required for a biological effect, and the length of time that the biologically active substance has to be released for treatment. In certain embodiments, the biologically active substance may be blended with a polymer matrix at different loading levels, in one embodiment at room temperature and without the need for an organic solvent. In other embodiments, the compositions may be formulated as microspheres. In some embodiments, the compound may be formulated for sustained release.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, croscarmellose or its sodium salt, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al, 1980, Invest Ophthalmol Vis Sci 19(3): 308-13), which also works as preservative against microbial contamination.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

EXAMPLES

Example 1. Synthesis of 2-(5-amino-7-chloro-2-p-tolylbenzoxazol-6-yl)propan-2-ol (2)

3-Methoxy-4-(trifluoroacetylamino)benzoic acid (2-1)

To a suspension of 5.0 g 4-amino-3-methoxybenzoic acid in 200 mL EtOAc was added under stirring a solution of 5.0 mL $(CF_3CO)_2O$ in 50 mL of EtOAc. After complete addition, the reaction mixture was further stirred at room temperature for 2 h. The solution was filtered, and the filtrate was evaporated to dryness. The residue was dissolved and evaporated twice in EtOAc. The final residue was dried under high vacuum to afford pure (2-1) as a white solid.

5-Methoxy-2-nitro-4-(trifluoroacetylamino)benzoic acid (2-2)

A suspension of 7.55 g (2-1) in 80 mL 96% $H_2SO_4$ was stirred at room temperature until a homogeneous solution was formed. The solution was cooled with an ice bath under stirring while a solution of 2.03 g 90.6% fuming $HNO_3$ in 20 mL 96% $H_2SO_4$ was added dropwise under cooling. The temperature was maintained below 10° C. After complete addition, the mixture was further stirred for 10 min, and then slowly added onto 200 g ice, under vigorous stirring. The mixture was saturated with NaCl and extracted with EtOAc (3×100 mL). The combined organic layer was washed with brine (2×50 mL), dried with $Na_2SO_4$, and then evaporated to give pure (2-2) as a light brown solid.

4-Amino-5-hydroxy-2-nitrobenzoic acid (2-3)

A mixture of 6.94 g (2-2) in 35 mL 20% aqueous NaOH was stirred under argon at 100° C. overnight. The mixture was cooled to room temperature. To it was added dropwise 20 mL 12 N HCl under ice bath cooling. After complete addition, the solution was evaporated, and the residue was extracted with 200 mL absolute EtOH. The solid NaCl was filtered off, and the filtrate was evaporated to give the crude HCl salt of (2-3) as a dark grey solid.

4-Amino-5-hydroxy-2-nitrobenzoic acid ethyl ester (2-4)

The above 6.95 g crude HCl salt of (2-3) was dissolved in 250 mL absolute EtOH. The solution was purged with dry HCl to nearly saturation, and then stirred at 80° C. for 36 h. Solvent was evaporated, and the residue was partitioned between 200 mL EtOAc and 200 mL brine. The aqueous layer was extracted with EtOAc (2×100 mL). The combined organic layer was dried with $Na_2SO_4$, acidified with 2 mL of HOAc, and then passed through a short silica gel column. The column was eluted with 1% HOAc/EtOAc. The combined yellow fraction was evaporated to give crude (2-4) as a red viscous oil.

5-Hydroxy-4-(4-methylbenzoylamino)-2-nitrobenzoic acid ethyl ester (2-5)

A mixture of 2.26 crude (2-4) and 2.1 g p-toluoyl chloride in 25 mL 1,4-dioxane was stirred at 95° C. for 1.5 h. Solvent was removed, and the residue was evaporated twice with EtOH and then evaporated twice with EtOAc. The final residue was dried at 60° C. under high vacuum to give crude (2-5) as a tan solid.

2-Chloro-3-hydroxy-4-(4-methylbenzoylamino)-6-nitrobenzoic acid ethyl ester (2-6)

A suspension of 3.35 g (2-5) in 100 mL dioxane was stirred until a clear solution was formed, and then 70 pit diisopropylamine (DIPA) was added. The solution was stirred at 50° C. while 1.96 mL $SO_2Cl_2$ was added. The reaction mixture was stirred under argon at 50° C. for 1 h, cooled to room temperature, diluted with 200 mL EtOAc, washed with water (3×100 mL), and dried with $MgSO_4$.

Solvent was evaporated and the residue was dried at 60° C. under high vacuum to give crude (2-6) as a brown solid.

7-Chloro-5-nitro-2-(p-tolyl)benzoxazole-6-carboxylic acid ethyl ester (2-7)

A mixture of 4.35 g crude (2-6) and 3.93 g Ph₃P in 50 mL dry THF was stirred at room temperature until a solution was formed. To it was added 6.7 mL 40% DEAD/toluene, and the mixture was stirred at 70° C. for 1 h. The mixture was diluted with 50 mL EtOH and evaporated. The residue was separated by silica gel column chromatography with hexane-EtOAc as eluent to give pure (2-7) as a white solid.

5-Amino-7-chloro-2-(p-tolyl)benzoxazole-6-carboxylic acid ethyl ester (2-8)

A mixture of 1.17 g (2-7), 1.07 g iron powder and 25 mL glacial HOAc was heated at 60° C. under vigorous stirring for 3 h. The reaction mixture was diluted with 200 mL EtOAc. The slurry was passed through a celite pellet, and the celite was washed with EtOAc. The combined filtrates were passed through a short silica gel column, and the column was eluted with EtOAc. The combined yellow fractions were evaporated, and the residue was crystallized from hexanes-EtOAc to give pure (2-8) as a bright yellow solid.

2-(5-Amino-7-chloro-2-(p-tolyl)benzoxazol-6-yl)propan-2-ol (2)

A mixture of 7.0 mL 3.0 M MeMgCl/THF and 6 mL THF was protected under argon, and cooled in an ice bath with vigorous stirring. To it was added dropwise a solution of 886 mg (2-8) in 50 mL THF. After complete addition, the mixture was stirred at 0° C. for 5 min. To the mixture was added 100 mL saturated $NH_4Cl$ with ice bath cooling and vigorous stirring. The organic layer was separated, and the aqueous layer was extracted with $CH_2Cl_2$ (DCM) (3×100 mL). The combined organic layers were dried with $MgSO_4$ and evaporated. The crude product was purified by silica gel column chromatography with MeOH-DCM as eluent and then crystallized from heptane/DCM to give pure (2) as an off-white solid.

$^1$H NMR (400 MHz, CDCl₃) δ: 1.89 (s, 6H), 2.41 (s, 3H), 4.45 (br, 3H, $NH_2$ and OH), 6.81 (s, 1H), 7.27 (d, 1H, J=8.8 Hz), 8.07 (d, 1H, J=8.4 Hz).

$^{13}$C NMR (100 MHz, CDCl₃) δ: 21.7, 31.0, 76.9, 106.2, 113.5, 124.0, 126.8, 127.6, 129.6, 140.9, 142.2, 142.9, 145.3, 164.1.

LC-MS: 317.0 $(MH)^+$, 319.0 $[(M+2)H]^+$.

Apparent second order rate constant of RAL depletion: $k_{app}$: 24,700 $(M^{-1} \cdot h^{-1})$ Apparent equilibrium constant of RAL depletion: $K_{app}$: $2.29 \times 10^6$ Apparent free energy change of RAL depletion: $\Delta G_{app}$: −9.0 (kcal/mol)

Example 2. Synthesis of 2-(5-amino-7-chloro-2-phenylbenzoxazol-6-yl)propan-2-ol (3)

4-Benzoylamino-5-hydroxy-2-nitrobenzoic acid ethyl ester (3-1)

A mixture of 2.26 g crude 4-amino-5-hydroxy-2-nitrobenzoic acid ethyl ester (2-4) and 1.91 g benzoyl chloride in 25 mL 1,4-dioxane was stirred at 95° C. for 1 h. Solvent was removed and the residue was evaporated twice with EtOH. The residue was further evaporated twice with EtOAc, and then was dried at 60° C. under high vacuum to give crude (3-1) as a tan solid.

4-Benzoylamino-2-chloro-3-hydroxy-6-nitrobenzoic acid ethyl ester (3-2)

A suspension of 3.23 g (3-1) in 100 mL dioxane was stirred until a clear solution was formed. To it was added 70 μL DIPA, and the solution was stirred to 50° C., followed by addition of 2.03 mL $SO_2Cl_2$. The Reaction mixture was stirred under argon at 50° C. for 1 h, cooled to room temperature, diluted with 200 mL EtOAc, washed with water (3×100 mL), and then dried with $MgSO_4$. Solvent was evaporated and the residue was dried at 60° C. under high vacuum to give crude (3-2) as a brown solid.

7-Chloro-5-nitro-2-phenylbenzoxazole-6-carboxylic acid ethyl ester (3-3)

A mixture of crude 3.74 g (3-2) and 3.93 g Ph₃P in 50 mL dry THF was stirred at room temperature until a solution was formed. To it was added 6.7 mL 40% DEAD/toluene, and the mixture was stirred at 70° C. for 1 h. The mixture was diluted with EtOH and evaporated. The residue was separated by silica gel column chromatography with hexane-EtOAc as eluent to give (3-3) as a white solid.

5-Amino-7-chloro-2-phenylbenzoxazole-6-carboxylic acid ethyl ester (3-4)

A mixture of 0.89 g (3-3), 2.0 g iron powder and 25 mL glacial HOAc was heated at 60° C. under vigorous stirring for 1.5 h. The mixture was diluted with 200 mL EtOAc. The slurry was passed through a celite pellet, and the celite was washed with EtOAc. The combined filtrates were pass through a short silica gel column, and the column was eluted with EtOAc. The combined yellow fractions were evaporated, and the residue was crystallized from hexanes-EtOAc to give pure (3-4) as a bright yellow solid.

2-(5-Amino-7-chloro-2-phenylbenzoxazol-6-yl)propan-2-ol (3)

A mixture of 6 mL 3.0 M MeMgCl/THF and 6 mL THF was protected under argon, and cooled in an ice bath with vigorous stirring. To it was added dropwise a solution of 638 mg (3-4) in 50 mL THF. After complete addition, the mixture was stirred at 0° C. for 5 min. To the mixture was added 100 mL saturated $NH_4Cl$ with cooling and vigorous stirring. The organic layer was separated, and the aqueous layer was extracted with DCM (3×100 mL). The combined organic layers were dried with $MgSO_4$ and evaporated. The crude product was purified by silica gel column chromatography with MeOH-DCM as eluent, and then crystallized from heptane-DCM to give pure (3) as a pale yellow solid.

$^1$H NMR (400 MHz, CDCl₃) δ: 1.92 (s, 6H), 4.69 (br, 3H, $NH_2$ and OH), 6.87 (s, 1H), 7.48-7.54 (3H), 8.21 (m, 2H).

$^{13}$C NMR (100 MHz, CDCl₃) δ: 31.0, 77.0, 106.3, 113.6, 126.8, 126.9, 127.7, 128.9, 131.6, 140.9, 143.0, 145.4, 163.9.

LC-MS: 303.1 $(MH)^+$, 305.0 $[(M+2)H]^+$.

Apparent second order rate constant of RAL depletion: $k_{app}$: 21,600 $(M^{-1} \cdot h^{-1})$ Apparent equilibrium constant of RAL depletion: $K_{app}$: $7.14 \times 10^6$ Apparent free energy change of RAL depletion: $\Delta G_{app}$: −9.7 (kcal/mol)

Example 3. Synthesis of 2-(6-amino-4-chloro-3-cyclopropylbenzisoxazol-5-yl)propan-2-ol (4)

(2-Chloro-4,6-dimethoxyphenyl)cyclopropylmethanone (4-1)

A solution of 28.28 g 1-chloro-3,5-dimethoxybenzene and 17.8 mL cyclopropanecarbonyl chloride in 300 mL dry 1,2-dichloroethane (DCE) was protected with argon, and cooled in a dry ice/acetone bath to −30 to −40° C. To it was added in portions 32.4 g $AlCl_3$ powder under vigorous stirring. After complete addition, the solution was stirred at −30 to −40° C. for 30 min, and then allowed to warm up to room temperature. After further stirring at room temperature for 20 min, the mixture was added onto 1 kg ice under stirring. The mixture was extracted with ether (3×300 mL). The combined organic layers were dried with $MgSO_4$ and evaporated. The residue was separated by column chromatography with hexanes/EtOAc as eluent to give pure (4-1) as a white solid.

(2-Chloro-6-hydroxy-4-methoxyphenyl)cyclopropylmethanone (4-2)

A solution of 13.45 g (4-1) in 100 mL dry DCM was protected with argon, and cooled at −78° C. (dry ice/acetone bath) under stirring. To it was added 62 mL 1 M $BBr_3$/DCM. After complete addition, the mixture was further stirred at −78° C. for 1 h. To the mixture was slowly injected 50 mL MeOH under dry ice/acetone bath cooling and vigorous stirring. After complete injection, the mixture was further stirred at −78° C. for 10 min, and then allowed to warm up to room temperature. The mixture was partitioned between 500 mL DCM and 500 mL brine. The organic layer was separated, washed with brine (2×100 mL), and then mixed with a solution of 4.0 g NaOH in 300 mL water. After stirring at room temperature for 1 h, the mixture was acidified with 10 mL 12 N aqueous HCl with stirring. The organic layer was separated, dried with $MgSO_4$, and evaporated. The residue was separated by silica gel column chromatography with hexanes-EtOAc as eluent to give (4-2) as a white solid.

(E)- and (Z)-(2-Chloro-6-hydroxy-4-methoxyphenyl)cyclopropylmethanone oxime (4-3)

A mixture of 10.38 g (4-2) and 15.95 g $NH_2OH \cdot HCl$ in 150 mL dry pyridine was protected under argon, and stirred at 80° C. for 20 h. Solvent was evaporated, and the residue was partitioned between 400 mL 0.1 N HCl/brine and 400 mL $Et_2O$. The organic layer was separated, washed with water (2×50 mL), dried with $MgSO_4$ and evaporated. The residue was crystallized from heptane-EtOAc to give pure (4-3) as a white solid.

(E)- and (Z)-(2-Chloro-6-hydroxy-4-methoxyphenyl)cyclopropylmethanone O-acetyl oxime (4-4)

To a suspension of 9.75 g (4-3) in 40 mL EtOAc was added 6.5 mL $Ac_2O$ under stirring at room temperature. After complete addition, the mixture was stirred at room temperature for 1 h. To it was added 50 mL MeOH and 20 mL pyridine, and the mixture was stirred at room temperature for 30 min. Solvent was evaporated, and the residue was partitioned between 300 mL 1 N HCl/brine and 300 mL EtOAc. The organic layer was separated, washed with water (2×50 mL), dried with $MgSO_4$ and evaporated to give crude (4-4) as a light brown oil.

4-Chloro-3-cyclopropyl-6-methoxybenzisoxazole (4-5)

Crude (4-4) was protected under argon, and heated in an oil bath at 150° C. for 3 h. The crude product was purified by silica gel column chromatography using hexanes-EtOAc as eluent to give pure (4-5) as a light tan solid.

4-Chloro-3-cyclopropylbenzisoxazol-6-ol (4-6)

A solution of 7.61 g (4-5) in 75 mL dry DCM was protected under argon, and cooled to 78° C. in a dry ice/acetone bath. To it was added dropwise 80 mL 1 M $BBr_3$ in DCM with vigorous stirring. After complete addition, the mixture was allowed to warm to room temperature, and then stirred at room temperature for 1 h. The mixture was again cooled to 78° C. in a dry ice/acetone bath. To it was added 20 mL MeOH under vigorous stirring. After complete addition, the reaction mixture was allowed to warm to room temperature, and then partitioned between 1.5 L brine and 1.5 L EtOAc. The organic layer was separated, and the aqueous layer was extracted with EtOAc (2×300 mL). The combined organic layers were dried with $MgSO_4$, and passed through a short silica gel column that was eluted with EtOAc. The combined fractions were evaporated to give pure (4-6) as a light brown oil, which solidified upon standing.

4-Chloro-3-cyclopropylbenzisoxazol-6-yl trifluoromethanesulfonate (4-7)

A mixture of 6.88 g (4-6) and 4 mL pyridine in 50 mL DCM was protected under argon and stirred at 0° C. in an ice bath. To it was added dropwise 6.73 mL $Tf_2O$ with vigorous stirring. After complete addition, the mixture was allowed to warm up to room temperature. After further stirring for 10 min at room temperature, the mixture was partitioned between 200 mL 1 N HCl and 300 mL DCM. The organic layer was separated, washed sequentially with 100 mL 1 N HCl, 100 mL brine, 100 mL 5% aqueous $NaHCO_3$ and 100 mL brine, dried with $MgSO_4$ and then evaporated. The residue was purified by column chromatography with hexanes-EtOAc as eluent to give pure (4-7) as an off-white solid.

tert-Butyl(4-chloro-3-cyclopropylbenzisoxazol-6-yl) carbamate (4-8)

A mixture of 8.02 g (4-7), 2.87 g tert-butyl carbamate, 2.37 g tBuONa, 1.08 g tris(dibenzylideneacetone)dipalladium(0) ($Pd_2dba_3$), 2.0 g 2-di-tert-butylphosphino-2',4',6'-triisopropylbiphenyl(t-butyl Xphos) and 7 g 4 Å molecular sieves in 120 mL dry toluene was purged with argon, and then heated at 110° C. with vigorous stirring for 20 min. The reaction mixture was diluted with 300 mL EtOAc, and passed through a celite pellet which was then washed with EtOAc. The combined solutions were evaporated and the residue was separated by silica gel column chromatography with hexanes-EtOAc as eluent to give crude (4-8) as a light brown oil.

6-Amino-4-chloro-3-cyclopropylbenzisoxazole (4-9)

The 4.09 g crude (4-8) was dissolved in 10 mL DCM, followed by addition of 10 mL TFA. The mixture was stirred at room temperature for 30 min. Solvent was removed, and the residue was partitioned between 200 mL DCM and 200 mL 10% NaHCO$_3$. The organic layer was separated, washed with water (2×50 mL), dried with MgSO$_4$ and evaporated. The residue was separated by silica gel column chromatography with hexanes-EtOAc as eluent to give pure (4-9) as a white solid.

5-Bromo-4-chloro-3-cyclopropyibenzisoxazol-6-ylamine (4-10) and 7-bromo-4-chloro-3-cyclopropylbenzisoxazol-6-ylamine (6-1)

To a solution of 1.96 g (4-9) in 100 mL DCM was added 1.67 g solid NBS in small portions under vigorous stirring at room temperature. After complete addition, the mixture was further stirred at room temperature for 30 min, diluted with 100 mL DCM, washed sequentially with 10% aqueous NaHSO$_3$ (200 mL) and water (2×200 mL), dried with MgSO$_4$, and evaporated to give a 1:1 mixture of (4-10) and (6-1) as a tan oil, which solidified on standing.

6-Amino-4-chloro-3-cyclopropylbenzisoxazole-5-carbonitrile (4-11) and 6-amino-4-chloro-3-cyclopropylbenzisoxazole-7-carbonitrile (6-2)

A suspension of 2.72 g of a mixture of (4-10) and (6-1), 1.70 g CuCN and 3.62 g CuI in 25 mL dry DMF was purged with argon, and then heated at 110° C. in an oil bath with vigorous stirring for 15 h. The mixture was cooled to room temperature. To it was added 100 mL 30% aqueous NH$_3$. After stirring at room temperature for 1 h, the mixture was diluted with 300 mL water, and extracted with EtOAc (2×500 mL). The combined organic layers were washed with water (3×200 mL), dried with MgSO$_4$ and evaporated. The residue was separated by silica gel column chromatography with hexanes-EtOAc as eluent to give (4-11) as a light yellow solid, and (6-2) as a light tan solid.

4-Chloro-5-cyano-3-cyclopropyl-6-(tritylamino)benzisoxazole (4-12)

To a mixture of 435 mg (4-11) and 700 µL TEA in 20 mL DCM was added 1.09 g solid trityl chloride in small portions under stirring at room temperature. After complete addition, the mixture was further stirred at room temperature for 30 min. The reaction mixture was diluted with 300 mL DCM, washed with water (4×200 mL), dried with MgSO$_4$ and then evaporated. The residue was separated by silica gel column chromatography with DCM as eluent to give pure (4-12) as a white solid.

4-Chloro-3-cyclopropyl-6-(tritylamino)benzisoxazole-5-carbaldehyde (4-13)

A solution of 481 mg (4-12) in 13 mL dry THF was cooled in an ice bath with stirring. To it was added dropwise 7 mL 1 M DIBAL/toluene. After complete addition, the reaction mixture was stirred at 0° C. for 2.5 h. The reaction was quenched with 100 mL 1% aqueous tartaric acid, and the mixture was extracted with DCM (3×100 mL). The organic layer was washed with water (3×100 mL), dried with MgSO$_4$ and evaporated. The residue was dissolved in DCM and adsorbed onto silica gel. The mixture was air-dried and separated by silica gel column chromatography with hexanes-EtOAc as eluent to give crude (4-13) as a yellow solid.

1-[4-Chloro-3-cyclopropyl-6-(tritylamino)benzisoxazol-5-yl]ethanol (4-14)

The above 257.8 mg crude (4-13) was dissolved in 10 mL dry THF, and the solution was added to a mixture of 2.0 mL 3 M MeMgCl/THF and 2 mL dry THF at 0° C. (ice bath) with stirring. After complete addition, the mixture was further stirred at 0° C. for 5 min, and then quenched with 100 mL 5% NH$_4$Cl under ice bath cooling. The mixture was extracted with DCM (3×100 mL), dried with MgSO$_4$ and evaporated. The residue was separated by silica gel column chromatography with hexanes-EtOAc as eluent to give pure (4-14) as a white solid.

1-[4-Chloro-3-cyclopropyl-6-(tritylamino)benzisoxazol-5-yl]ethanone (4-15)

To a solution of 150.5 mg (4-14) in 20 mL dry DCM was added 271 mg solid Dess-Martin period inane (1,1,1-triacetoxy-1,1-dihydro-1,2-benziodoxol-3(1H)-one, DMP) in small portions at room temperature under vigorous stirring. After complete addition, the reaction mixture was further stirred at room temperature for 10 min. The reaction mixture was diluted with 300 mL DCM, washed with water (4×200 mL), dried with MgSO$_4$ and evaporated. The residue was separated by silica gel column chromatography with hexanes-EtOAc as eluent to give pure (4-15) as a pale yellow solid.

1-(6-Amino-4-chloro-3-cyclopropylbenzisoxazol-5-yl)ethanone (4-16)

To a solution of 182 mg (4-15) in 20 mL dry DCM was added dropwise 2 mL TFA under stirring at room temperature. The solution was stirred at room temperature for 10 min, diluted with 200 mL DCM, washed with water (4×100 mL), dried with MgSO$_4$ and evaporated to give crude (4-16) as a white solid.

2-(6-Amino-4-chloro-3-cyclopropylbenzisoxazol-5-yl)propan-2-ol (4)

The 174.7 mg crude (4-16) was dissolved in 20 mL dry THF, and the solution was added dropwise to a well stirred mixture of 2.5 mL 3M MeMgCl/THF and 2 mL THF at 0° C. (ice bath). After complete addition, the mixture was further stirred at 0° C. for 5 min. To it was added dropwise 100 mL 5% aqueous NH$_4$Cl under ice bath cooling and stirring. The mixture was extracted with DCM (3×100 mL), dried with MgSO$_4$ and evaporated. The crude product was purified by silica gel column chromatography with MeOH-DCM as eluent and then crystallized from heptane-DCM to give pure (4) as a white solid.

$^1$H NMR (400 MHz, CDCl$_3$) δ: 1.10 (m, 2H), 1.20 (m, 2H), 1.91 (s, 6H), 2.18 (m, 1H), 4.28 (br, 2H, NH$_2$), 6.57 (s, 1H).

$^{13}$C NMR (100 MHz, CDCl$_3$) δ: 8.68, 9.35, 30.0, 77.4, 97.4, 121.2, 125.1, 133.1, 145.7, 149.3, 166.4.

LC-MS: 266.9 (MH)$^+$, 269.0 [(M+2)H]$^+$.

Apparent second order rate constant of RAL depletion: $k_{app}$: 31,700 (M$^{-1}$·h$^{-1}$)

Apparent equilibrium constant of RAL depletion: $K_{app}$: >2×10$^7$

Apparent free energy change of RAL depletion: $\Delta G_{app}$: <−10 (kcal/mol)

Example 4. Synthesis of 2-(6-amino-4-chloro-3-cyclopropylbenzisoxazol-7-yl)propan-2-ol (6)

1-(6-Amino-4-chloro-3-cyclopropyl-benzisoxazol-7-yl)ethanone (6-3)

To a mixture of 636 mg (6-2) and 43 mg CuI was slowly added 8.16 mL 3 M MeMgCl/THF under stirring and ice bath cooling. The suspension was protected under argon, and heated at 70° C. in an oil bath for 15 min. The mixture was cooled to 0° C. in an ice bath. To it was added 136 mL MeOH, followed by 2.17 g solid NH$_4$Cl and 13.6 mL water. The mixture was warmed to room temperature with stirring to give a clear solution, which was adsorbed on silica gel, air-dried and separated by silica gel column chromatography with hexanes-EtOAc as eluent to give (6-3) as a yellow solid.

2-(6-Amino-4-chloro-3-cyclopropylbenzisoxazol-7-yl)propan-2-ol (6)

A mixture of 1.54 mL 3 M MeMgCl/THF and 5 mL dry THF was protected under argon and stirred with ice bath cooling. To it was added a solution of 387.1 mg (6-3) in 15 mL dry THF under vigorous stirring. After complete addition, the solution was further stirred at 0° C. for 20 min. To it was added 100 mL saturated aqueous NH$_4$Cl with ice bath cooling and vigorous stirring. The mixture was warmed to room temperature and extracted with DCM (3×100 mL). The combined organic layers were dried with MgSO$_4$ and evaporated. The crude product was purified by silica gel column chromatography with MeOH-DCM as eluent, and crystallized from heptane-DCM to give pure (6) as a light tan solid.

$^1$H NMR (400 MHz, CDCl$_3$) δ: 1.12 (m, 2H), 1.18 (m, 2H), 1.78 (s, 6H), 2.17 (m, 1H), 4.86 (br, 2H, NH$_2$), 6.60 (s, 1H).

$^{13}$C NMR (100 MHz, CDCl$_3$) δ: 8.81, 9.26, 30.1, 74.1, 112.7, 114.4, 121.8, 131.3, 143.8, 148.6, 166.1.

LC-MS: 267.0 (MH)$^+$, 268.9 [(M+2)H]$^+$.

Apparent second order rate constant of RAL depletion: k$_{app}$: 12,700 (M$^{-1}$·h$^{-1}$)

Apparent equilibrium constant of RAL depletion: K$_{app}$: 3.35×10$^6$

Apparent free energy change of RAL depletion: ΔG$_{app}$: −9.2 (kcal/mol)

Example 5. Synthesis of 2-(5-amino-7-chloro-3-cyclopropylbenzisoxazol-6-yl)propan-2-ol (5)

Cyclopropanecarboxylic acid methoxymethylamide (5-1)

A suspension of 9.75 g N,O-dimethylhydroxylamine hydrochloride and 9.7 mL pyridine in 200 mL DCM was stirred at room temperature for 10 min, and then cooled in an ice bath with stirring. To it was added dropwise a solution of 9.03 mL cyclopropanecarbonyl chloride in 40 mL DCM with vigorous stirring. After complete addition, the mixture was stirred at 0° C. for 30 min, and then at room temperature for 1 h. The solution was diluted with 100 mL DCM, washed with brine (3×200 mL), and dried with MgSO$_4$. Solvent was evaporated, and the residue vacuum distilled. The fraction collected at 43-45° C./1 mmHg gave (5-1) as a colorless liquid.

2-(3-Chloro-4-fluorophenyl)-1,1,1,3,3,3-hexamethyldisilazane (5-2)

A solution of 7.3 g 3-chloro-4-fluoroaniline in 100 mL dry THF was protected under argon and cooled at −78° C. (dry ice/acetone bath). To it was slowly added 21 mL 2.5 M nBuLi in hexanes with vigorous stirring. After complete addition, the suspension was further stirred at −78° C. for 10 min. To the latter was slowly added 6.65 mL chlorotrimethylsilane (TMSCl) under vigorous stirring. After complete addition, the mixture was further stirred at −78° C. for 30 min. To the latter was again added 24 mL 2.5 M nBuLi, followed by 7.65 mL TMSCl under vigorous stirring. The mixture was stirred at −78° C. for 30 min, and then allowed to warm to room temperature. Solvent was removed and the residue was vacuum distilled. The fractions collected below 95° C./1 mmHg were pooled to give (5-2) as a colorless liquid.

(5-Amino-3-chloro-2-fluorophenyl)(cyclopropyl)methanone (5-3)

A solution of 9.11 g (5-2) in 100 mL dry THF was cooled to −78° C. in a dry ice/acetone bath under argon. To it was added dropwise 15.7 mL 2.5 M nBuLi in hexanes under vigorous stirring. After complete addition, the mixture was stirred at −78° C. for 2 h. To it was added slowly 5.2 g (5-1) under stirring. After complete addition, the reaction mixture was stirred at −78° C. for 1 h, and then allowed to warm up to room temperature. The reaction mixture was poured into 400 mL cold 1:1 MeOH/1 N HCl under stirring. After further stirring for 30 min, the mixture was extracted with DCM (3×200 mL). The combined organic layers were dried with MgSO$_4$ and evaporated to give crude (5-3) as a light brown oil.

N-[3-Chloro-5-(cyclopropylcarbonyl)-4-fluorophenyl]acetamide (5-4)

Crude (5-3) (6.09 g) was dissolved in 100 mL DCM. To it were added sequentially 6 mL acetic anhydride (Ac$_2$O) and 9.6 mL triethylamine (TEA) with ice bath cooling and vigorous stirring. After complete addition, the reaction mixture was further stirred at room temperature for 1 h, diluted with 200 mL DCM, and washed with 0.1 N HCl (3×200 mL). The organic layer was dried with MgSO$_4$ and evaporated. The crude product was purified by silica gel column chromatography with hexanes-EtOAc as eluent and then crystallized from hexanes-EtOAc to give pure (5-4) as a white solid.

(E)- and (Z)-N-{3-Chloro-5-[cyclopropyl(hydroxyimino)methyl]-4-fluorophenyl}acetamide (5-5)

A mixture of 2.28 g (5-4), 3.1 g NH$_2$OH.HCl, 30 mL pyridine and 30 mL EtOH was stirred at 50° C. for 22 h. EtOH was evaporated, and the residue was partitioned between 200 mL Et$_2$O and 200 mL 1 N HCl/brine. The organic layer was separated, washed with water (2×20 mL), dried with MgSO$_4$ and evaporated to give pure (5-5) as an off-white amorphous solid.

N-(7-Chloro-3-cyclopropylbenzisoxazol-5-yl)acetamide (5-6)

A solution of 2.01 g (5-5) in 40 mL dry DMF was protected with argon and stirred with ice bath cooling. To it was added in portions 1.48 g 60% NaH in mineral oil under vigorous stirring. After complete addition, the reaction mixture was stirred at room temperature for 1.5 h, and then was carefully added into a mixture of 300 mL saturated NaHCO$_3$ and 300 mL EtOAc under stirring. The organic layer was separated, washed with water (3×50 mL), dried with MgSO$_4$ and evaporated. The residue was separated by column chromatography with hexanes-EtOAc as eluent to give pure (5-6) as a white solid.

tert-Butyl acetyl(7-chloro-3-cyclopropylbenzisoxazol-5-yl)carbamate (5-7)

A mixture of 789.3 mg (5-6), 808 mg Boc$_2$O and 38 mg DMAP in 40 mL dry DCM was stirred at room temperature for 1 h. Solvent was evaporated to give crude (5-7) as a white solid.

tert-Butyl(7-chloro-3-cyclopropylbenzisoxazol-5-yl)carbamate (5-8)

The above crude (5-7) was dissolved in 100 mL MeOH. The solution was basified with 0.1 mL 25 wt. % NaOMe/MeOH, and then stirred at room temperature for 30 min. To the solution was added 1 g solid NH$_4$Cl, and the solvent was evaporated. The residue was partitioned between 300 mL 0.1 N HCl/brine and 300 mL EtOAc. The organic layer was separated, washed sequentially with 100 mL 0.1 N HO/brine, 100 mL water, 100 mL saturated NaHCO$_3$ and 100 mL water, dried with MgSO$_4$ and evaporated. The residue was crystallized from heptane-EtOAc to give pure (5-8) as a white solid.

5-[(tert-Butoxycarbonyl)amino]-7-chloro-3-cyclopropylbenzisoxazole-6-carboxylic acid (5-9)

A solution of 770 mg (5-8) in 50 mL dry THF was protected under argon, and stirred with dry ice/acetone bath cooling. To it was added dropwise 5.9 mL 1.7 M tBuLi/pentane under vigorous stirring. After complete addition, the mixture was further stirred at −78° C. for 5 min. To the latter was added all at once 7.2 g freshly crushed dry ice under vigorous stirring. The mixture was stirred at −78° C. for 5 min, and then allowed to warm up to room temperature. The reaction mixture was partitioned between 300 mL 1 N HCl/brine and 300 mL EtOAc. The organic layer was separated, washed with 100 mL 0.1 N HCl/brine, dried with MgSO$_4$ and evaporated. The residue was separated by silica gel column chromatography with hexanes/EtOAc/HOAc as eluent to give (5-9) as an off-white foam.

Methyl 5-[(tert-butoxycarbonyl)amino-7-chloro-3-cyclopropylbenzisoxazole-6-carboxylate (5-10)

A solution of 815 mg (5-9) and 5 mL MeOH in 10 mL DCM was stirred with ice bath cooling. To it was added dropwise 2.31 mL 2 M trimethylsilyldiazomethane (TM-SCHN$_2$) in hexanes under stirring. After complete addition, the solution was stirred at room temperature for 10 min and evaporated. The residue was dissolved in 100 mL DCM, and the solution was passed through a short silica gel column. The column was eluted with MeOH-DCM, and the combined fractions were evaporated to give (5-10) as an off-white solid.

Methyl 5-amino-7-chloro-3-cyclopropylbenzisoxazole-6-carboxylate (5-11)

A solution of 813 mg (5-10) in 10 mL DCM was stirred with ice bath cooling. To it was added dropwise 10 mL TFA with stirring. After complete addition, the mixture was stirred at room temperature for 30 min and evaporated. The residue was partitioned between 200 mL saturated NaHCO$_3$ and 200 mL EtOAc. The organic layer was separated, washed with water (2×50 mL), dried with MgSO$_4$, and evaporated to give (5-11) as a yellow oil, which solidified on standing.

2-(5-Amino-7-chloro-3-cyclopropylbenzisoxazol-6-yl)propan-2-ol (5)

A solution of 7.73 mL 3M MeMgCl/THF in 6 mL dry THF was protected under argon and stirred with ice bath cooling. To it was added dropwise a solution of 620 mg (5-11) in 50 mL dry THF under vigorous stirring. After complete addition, the mixture was allowed to warm and then stirred at room temperature for 1 h. The mixture was added carefully into 300 mL saturated aqueous NH$_4$Cl under stirring and ice bath cooling. The mixture was extracted with DCM (3×100 mL), dried with MgSO$_4$ and evaporated. The crude product was purified by silica gel column chromatography with MeOH-DCM as eluent, and then crystallized from heptane-DCM to give pure (5) as an off-white solid.

$^1$H NMR (400 MHz, CDCl$_3$) δ: 1.10 (m, 2H), 1.15 (m, 2H), 1.91 (s, 6H), 2.09 (m, 1H), 4.33 (br, 3H, NH$_2$ and OH), 6.70 (s, 1H).

$^{13}$C NMR (100 MHz, CDCl$_3$) δ: 7.11, 7.25, 30.7, 77.1, 105.6, 113.7, 120.4, 132.5, 144.4, 155.4, 160.5.

LC-MS: 267.1 (MH)$^+$, 269.1 [(M+2)H]$^+$.

Apparent second order rate constant of RAL depletion: $k_{app}$: 35,300 (M$^{-1}$·h$^{-1}$)

Apparent equilibrium constant of RAL depletion: $K_{app}$: >2×10$^7$

Apparent free energy change of RAL depletion: $\Delta G_{app}$: <−10 (kcal/mol)

Example 6. Definition of Kinetic and Equilibrium Parameters

The parameters associated with the RAL depletion chemistry are as follows:

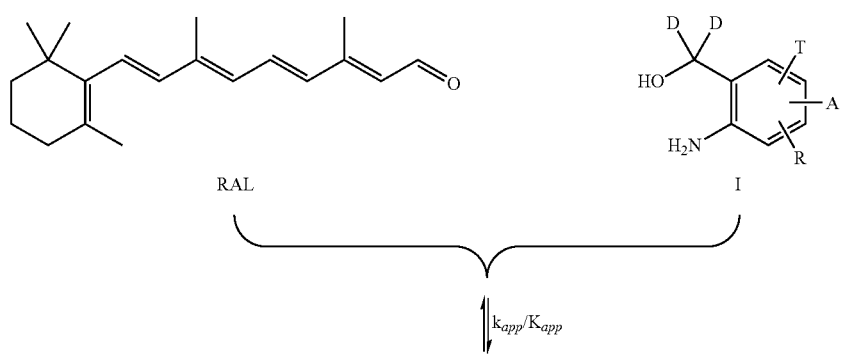

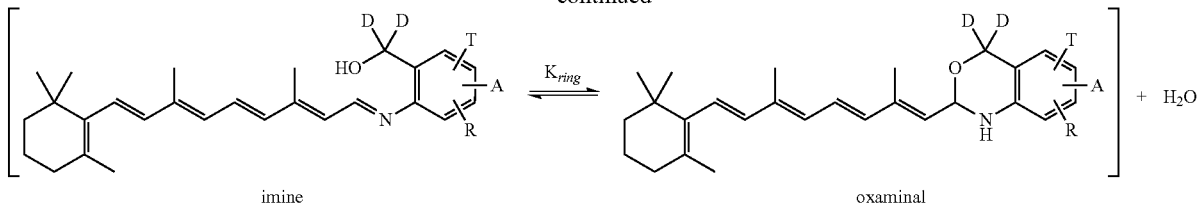

imine ⇌ oxaminal + H₂O $k_{app}$: apparent second order rate constant of RAL depletion by drug.
$K_{app}$: apparent equilibrium constant of RAL depletion by drug.

$$K_{app} = \frac{([imine]+[oxaminal])[H_2O]}{[RAL][drug]} \quad (1)$$

$\Delta G_{app}$: apparent free energy change of RAL depletion by drug.

$$\Delta G_{app} = -RT \ln K_{app} \quad (2)$$

$K_{ring}$: equilibrium constant of tautomerism from imine to oxaminal (ring closed).

$$K_{ring} = \frac{[oxaminal]}{[imine]} \quad (3)$$

$\Delta G_{ring}$: free energy change of tautomerism from imine to oxaminal (ring closed).

$$\Delta G_{ring} = -RT \ln K_{ring} \quad (4)$$

Example 7. Determination of $k_{app}$, $K_{app}$ and $\Delta G_{app}$ in Rod Outer Segments Frozen bovine rod outer segment preparation (64 μM of opsin) is thawed and vortexed thoroughly. A 200 μL aliquot of this sample is transferred into a 0.5 mL Eppendorf tube. To it is added 10 μL of 20 mM drug stock solution in EtOH, and the mixture is vortexed for 1 min. The tube is incubated at 37° C. in a Thermo Scientific microprocessor controlled 280 series water bath for 3 min before 5 μL freshly prepared 2.4 mM RAL solution in EtOH is added (the nominal starting concentrations of drug and RAL are 1.00 mM and 60 μM, respectively). After vortexing for 1 min, the tube is incubated at 37° C. over time. Aliquots of the reaction mixture (25 μL each) are taken periodically, and added onto 10 mg of solid NaBH₄ in a 0.5 mL Eppendorf tube. To the latter is added carefully 400 μL of 2:1 (v/v) EtOH/HOAc. The reduction mixture is vortexed for 1 min and centrifuged. The supernatant is separated, and analyzed by HPLC using a standard HPLC method:

Instrument: HPLC-PE-97
Column: Waters Sunfire $C_{18}$ 3.5 μm/4.6×100 mm column (Cat #186002553)
Solvent A: 0.05% HCOOH/95% HPLC grade water/5% HPLC grade MeCN
Solvent B: 0.05% HCOOH HPLC grade MeCN
Pump program: 0-3 min 5-100% B, 3-30 min 100% B, 31-32 min 100%-5% B, 32-35 min 5% B
Flow rate: 1 mL/min
Detector wavelengths: 329 and 250 nm
Reference wavelength: 400 nm
Injection volume: 50 μL.

The RAL depletion percentages are calculated by normalization of ROL and Re-RAL-drug peak integrals, which are then plotted against reaction time. Least squares fit of the RAL depletion plot according to pseudo-first order kinetics yields observed first order rate constant $k_{obsd}$, and $k_{app}$ is calculated according to $k_{obsd}=k_{app}[drug]$. $K_{app}$ is calculated from the equilibrium concentrations of free RAL, free drug and RAL-drug according to equation (1). $\Delta G_{app}$ was calculated according equation (2).

TABLE 1

RAL depletion by compounds in rod outer segment preparation containing 64 μM opsin at 37° C.

| Compound | $k_{app}$ (M⁻¹·h⁻¹)$^a$ | $K_{app}{}^b$ | $\Delta G_{app}$ (kcal/mol)$^c$ |
|---|---|---|---|
| Compound of WO 2006/127945 (Cl-quinoline-NH₂-OH) | 3,570 | 1.55 × 10⁵ | −7.4 |
| Compound of WO 2006/127945 (phenyl-benzoxazole-NH₂-OH) | 25,500 | 1.25 × 10⁶ | −8.6 |

TABLE 1-continued

RAL depletion by compounds in rod outer segment preparation containing 64 μM opsin at 37° C.

| Compound | $k_{app}$ (M$^{-1}$ · h$^{-1}$)$^a$ | $K_{app}^{b}$ | $\Delta G_{app}$ (kcal/mol)$^c$ |
|---|---|---|---|
| 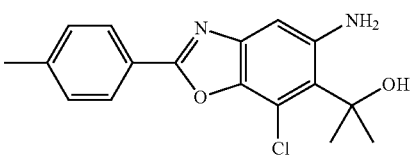 [SMILES: Cc1ccc(-c2nc3cc(N)c(C(C)(C)O)c(Cl)c3o2)cc1] (2) | 24,700 | 2.29 × 10$^6$ | −9.0 |
| 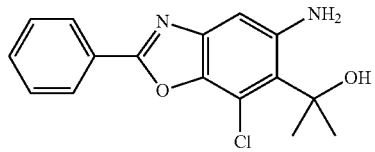 [SMILES: CC(C)(O)c1c(N)cc2nc(-c3ccccc3)oc2c1Cl] (3) | 21,600 | 7.14 × 10$^6$ | −9.7 |
| 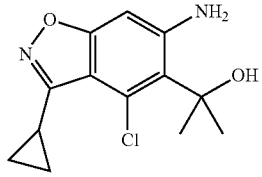 [SMILES: CC(C)(O)c1c(N)cc2onc(C3CC3)c2c1Cl] (4) | 31,700 | >2 × 10$^7$ | <−10 |
| 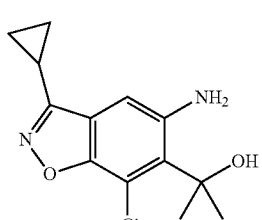 (5) | 35,300 | >2 × 10$^7$ | <−10 |
| 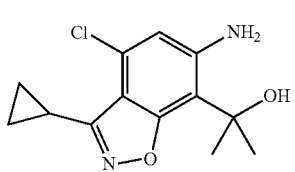 [SMILES: CC(C)(O)c1c(N)cc(Cl)c2c(C3CC3)noc12] (6) | 12,700 | 3.35 × 10$^6$ | −9.2 |

$^a$Apparent second order rate constant of RAL depletion.
$^b$Apparent equilibrium constant of RAL depletion.
$^c$Apparent free energy change of RAL depletion.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. A compound of formula (I):

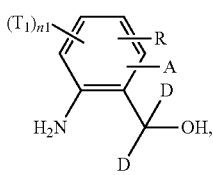
(I)

or a pharmaceutically acceptable salt thereof, wherein:

A and R are attached to adjacent carbon atoms on the phenyl ring, and together with the two carbon atoms to which they are attached, form a five-membered heteroaryl ring containing one nitrogen atom and one oxygen atom, wherein the heteroaryl ring is substituted with X;

X is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;

$n_1$ is 1 or 2;

$T_1$ is halogen; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from the group consisting of

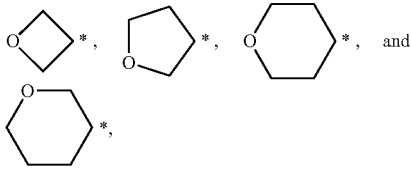

wherein "*" denotes the position of the carbon atom to which the two D are attached.

2. The compound of claim 1, wherein X is $C_3$-$C_6$ cycloalkyl, aryl, or aryl substituted with $C_1$-$C_6$ alkyl.

3. The compound of claim 1, wherein X is $C_1$-$C_{10}$ alkyl, or $C_1$-$C_{10}$ alkyl substituted with $C_3$-$C_6$ cycloalkyl.

4. The compound of claim 1, wherein each D is independently $C_1$-$C_6$ alkyl.

5. The compound of claim 4, wherein each D is methyl.

6. The compound of claim 1, wherein $n_1$ is 1.

7. The compound of claim 1, wherein the compound is of formula (Ia), (Ib), (Ic), or (Id):

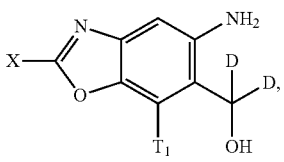
(Ia)

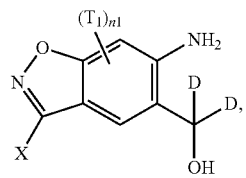
(Ib)

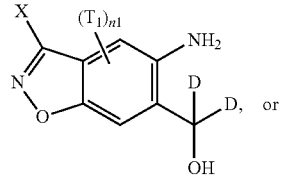
(Ic)

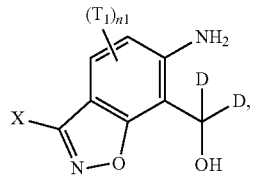
(Id)

or a pharmaceutically acceptable salt thereof, wherein:

X is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;

$n_1$ is 1 or 2;

each $T_1$ is independently F or Cl; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

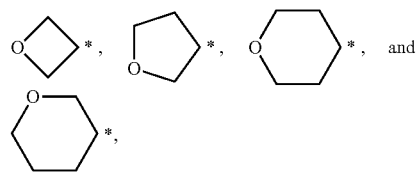

wherein "*" denotes the position of the carbon atom to which the two D are attached.

8. The compound of claim 7, wherein X is $C_3$-$C_6$ cycloalkyl, aryl, or aryl substituted with $C_1$-$C_6$ alkyl; each $T_1$ is independently F or Cl; and each D is methyl.

9. The compound of claim 8, wherein X is aryl, aryl substituted with methyl, or cyclopropyl; $n_1$ is 1; and $T_1$ is Cl.

10. The compound of claim 9, selected from the group consisting of:

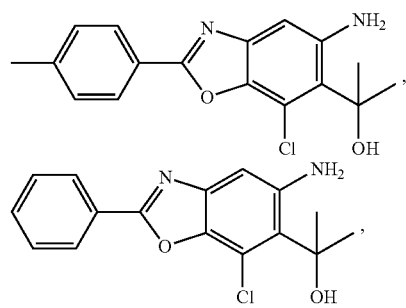

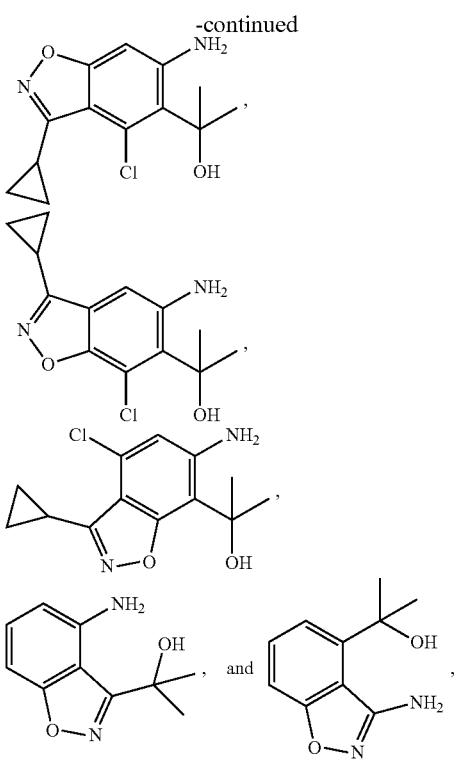

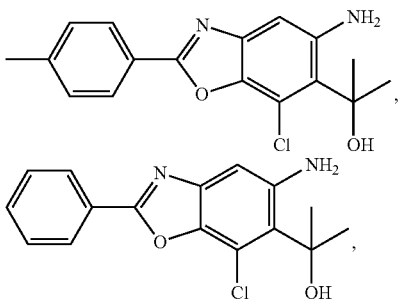

and a pharmaceutically acceptable salt thereof.

11. The compound of claim 8, selected from the group consisting of:

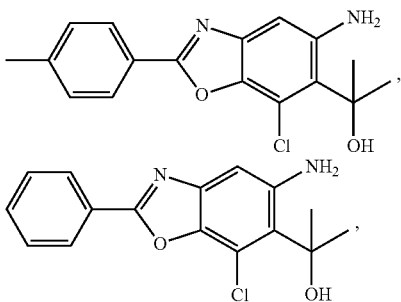

and a pharmaceutically acceptable salt thereof.

12. A pharmaceutical composition comprising a compound or a pharmaceutically acceptable salt thereof of claim 1, and a pharmaceutically acceptable carrier.

13. The pharmaceutical composition of claim 12, wherein the compound is selected from the group consisting of:

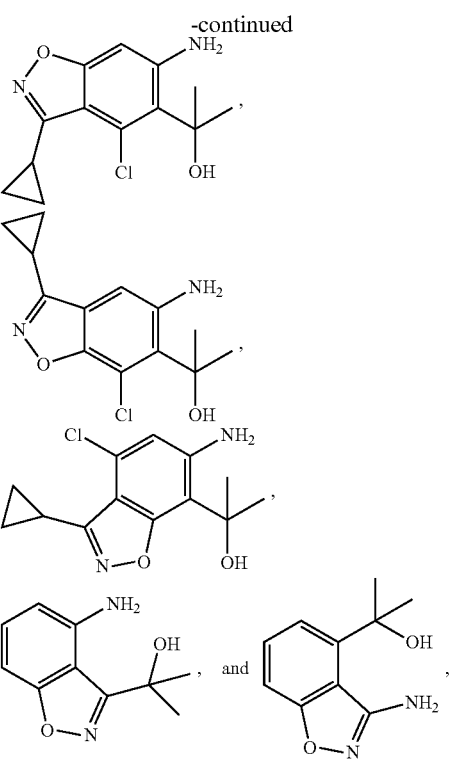

and a pharmaceutically acceptable salt thereof, and a pharmaceutically acceptable carrier.

14. A compound of formula (I):

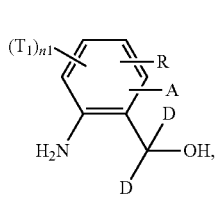

(I)

or a pharmaceutically acceptable salt thereof, wherein:

A and R are attached to adjacent carbon atoms on the phenyl ring, and together with the two carbon atoms to which they are attached, form a five-membered heteroaryl ring containing one nitrogen atom and one oxygen atom, wherein the heteroaryl ring is substituted with X;

X is $C_1$-$C_{10}$ alkyl, $C_1$-$C_{10}$ alkyl substituted with $C_3$-$C_6$ cycloalkyl, $C_3$-$C_6$ cycloalkyl, or aryl substituted with $C_1$-$C_6$ alkyl;

$n_1$ is 1 or 2;

each $T_1$ is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from the group consisting of

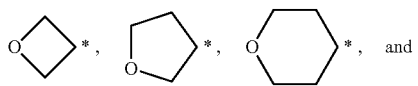

-continued

[structure: tetrahydropyran with *]

wherein "*" denotes the position of the carbon atom to which the two D are attached.

15. The compound of claim 14, wherein X is $C_3$-$C_6$ cycloalkyl or aryl substituted with $C_1$-$C_6$ alkyl.

16. The compound of claim 14, wherein X' is $C_1$-$C_{10}$ alkyl, or $C_1$-$C_{10}$ alkyl substituted with $C_3$-$C_6$ cycloalkyl.

17. The compound of claim 14, wherein each D is independently $C_1$-$C_6$ alkyl.

18. The compound of claim 17, wherein each D is methyl.

19. The compound of claim 14, wherein $n_1$ is 1.

20. The compound of claim 14, wherein $T_1$ is halogen.

21. The compound of claim 14, wherein the compound is of formula (Ia), (Ib), (Ic), or (Id):

[structure (Ia): benzoxazole with X, NH2, D, D, OH, T1]

[structure (Ib): isoxazole-fused with (T1)n1, NH2, D, D, OH, X]

[structure (Ic): isoxazole-fused with X, (T1)n1, NH2, D, D, OH, or]

[structure (Id): isoxazole-fused with (T1)n1, NH2, D, D, OH, X]

or a pharmaceutically acceptable salt thereof, wherein:

X is $C_1$-$C_{10}$ alkyl, $C_1$-$C_{10}$ alkyl substituted with $C_3$-$C_6$ cycloalkyl, $C_3$-$C_6$ cycloalkyl, or aryl substituted with $C_1$-$C_6$ alkyl;

$n_1$ is 1 or 2;

each $T_1$ is independently F, Cl, $C_1$-$C_{10}$ alkyl, $C_3$-$C_6$ cycloalkyl, $C_1$-$C_{10}$ alkyl substituted with $C_3$-$C_6$ cycloalkyl, or cyano; and each D is independently $C_1$-$C_6$ alkyl or $C_3$-$C_6$ cycloalkyl, or two D, together with the carbon atom to which they are attached, form a $C_3$-$C_6$ carbocyclic ring or a saturated heterocycle selected from

[structures: oxetane*, tetrahydrofuran*, tetrahydropyran*, and tetrahydropyran*]

wherein "*" denotes the position of the carbon atom to which the two D are attached.

22. The compound of claim 21, wherein X is $C_3$-$C_6$ cycloalkyl, or aryl substituted with $C_1$-$C_6$ alkyl; each $T_1$ is independently F, Cl, methyl, cyclopropyl, cyclobutyl, or cyano; and each D is methyl.

23. The compound of claim 22, wherein X is aryl substituted with methyl or cyclopropyl; $n_1$ is 1; and $T_1$ is Cl.

24. A pharmaceutical composition comprising a compound or a pharmaceutically acceptable salt thereof of claim 14, and a pharmaceutically acceptable carrier.

* * * * *